(12) United States Patent
Ip et al.

(10) Patent No.: US 11,779,321 B2
(45) Date of Patent: Oct. 10, 2023

(54) WOUND RETRACTOR AND DIFFUSER

(71) Applicant: Fisher & Paykel Healthcare Limited, Auckland (NZ)

(72) Inventors: Bernard Tsz Lun Ip, Auckland (NZ); Joseph Patrick Walter Strevens, Auckland (NZ); Jessica Rachel Fogarin, Auckland (NZ); Jonathan Stuart McFedries, Auckland (NZ); James Alexander Gordon, Auckland (NZ); Michael Joseph Blackhurst, Auckland (NZ); Jonathan David Harwood, Auckland (NZ); Ali Ghalib Abdul Rahman Ghalib, Auckland (NZ); Natalie May Robertson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 348 days.

(21) Appl. No.: 17/132,565

(22) Filed: Dec. 23, 2020

(65) Prior Publication Data

US 2021/0196257 A1 Jul. 1, 2021

Related U.S. Application Data

(63) Continuation of application No. 15/539,575, filed as application No. PCT/NZ2015/050219 on Dec. 23, 2015, now Pat. No. 10,925,591.

(Continued)

(51) Int. Cl.
A61B 17/02 (2006.01)
A61B 17/34 (2006.01)
A61B 90/40 (2016.01)

(52) U.S. Cl.
CPC .......... *A61B 17/0218* (2013.01); *A61B 17/02* (2013.01); *A61B 17/3423* (2013.01);
(Continued)

(58) Field of Classification Search
CPC . A61B 17/0218; A61B 17/02; A61B 17/3423; A61B 2090/401; A61B 2217/005; A61M 16/16
(Continued)

(56) References Cited

U.S. PATENT DOCUMENTS 3,881,477 A 5/1975 Von Otto
3,927,667 A 12/1975 Criddle et al.
(Continued)

FOREIGN PATENT DOCUMENTS

DE 102013101229 8/2014
WO WO 2006/094062 A1 9/2006
(Continued)

OTHER PUBLICATIONS

International Search Report and Written Opinion for PCT/NZ2015/050219 dated Jul. 4, 2016 in 23 pages.
(Continued)

*Primary Examiner* — Eduardo C Robert
*Assistant Examiner* — Tara Rose E Carter
(74) *Attorney, Agent, or Firm* — ) Knobbe Martens Olson & Bear LLP

(57) ABSTRACT

A diffuser for use with a wound retractor and configured to deliver gases includes an interface tube for connecting to a gases supply and a diffuser interface positioned at a proximal end of the interface tube, the diffuser interface configured for delivering gases received from the gases supply through the interface tube, and the diffuser interface comprising a diffusion mechanism configured to deliver gases in a diffusion direction. A wound retractor with an integrated diffuser is (Continued)

also disclosed. The wound retractor includes an upper ring, a lower ring, a sleeve extending between and connecting the upper ring to the lower ring, and an integrated diffuser interface having a gases inlet and a diffusion mechanism.

24 Claims, 25 Drawing Sheets

Related U.S. Application Data

(60) Provisional application No. 62/096,469, filed on Dec. 23, 2014.

(52) U.S. Cl.
CPC ............... *A61B 2017/0212* (2013.01); *A61B 2017/0225* (2013.01); *A61B 2017/349* (2013.01); *A61B 2017/3492* (2013.01); *A61B 2090/401* (2016.02); *A61B 2217/005* (2013.01)

(58) Field of Classification Search
USPC ................................................ 600/201–245
See application file for complete search history.

(56) References Cited

U.S. PATENT DOCUMENTS

| | | |
|---|---|---|
| 5,407,433 A | 4/1995 | Loomas |
| 5,735,791 A | 4/1998 | Alexander, Jr. et al. |
| 5,842,971 A | 12/1998 | Yoon |
| 5,849,005 A | 12/1998 | Garrison et al. |
| 6,494,858 B1 | 12/2002 | Van Der |
| 6,733,479 B1 | 5/2004 | Ott |
| 10,925,591 B2* | 2/2021 | Ip .................. A61M 13/003 |
| 2002/0022762 A1 | 2/2002 | Beane et al. |
| 2006/0247498 A1 | 11/2006 | Bonadio et al. |
| 2009/0118587 A1 | 5/2009 | Voegele et al. |
| 2010/0234794 A1 | 9/2010 | Weadock |
| 2010/0241061 A1 | 9/2010 | Ott et al. |
| 2010/0312066 A1* | 12/2010 | Cropper ............ A61B 17/3423 600/207 |
| 2013/0178709 A1* | 7/2013 | Suh .................... A61B 17/0218 600/205 |
| 2014/0163326 A1* | 6/2014 | Forsell .................... B25J 21/02 600/207 |
| 2014/0343366 A1* | 11/2014 | Coe .......................... A61M 1/85 600/205 |

FOREIGN PATENT DOCUMENTS

| | | |
|---|---|---|
| WO | WO 2013/106393 A1 | 7/2013 |
| WO | WO 2016/105214 | 6/2016 |

OTHER PUBLICATIONS

Biewenga E.D. et al., "An Innovative Wound Retractor/Protector for Prosthetic Urologic Surgery," Current Urology, vol. 6, Aug. 2012, pp. 205-208.

\* cited by examiner

WOUND RETRACTOR AND DIFFUSER

INCORPORATION BY REFERENCE TO ANY PRIORITY APPLICATIONS

This application is a continuation of U.S. patent application Ser. No. 15/539,575, filed Jun. 23, 2017, now U.S. Pat. No. 10,925,591, which is a U.S. National Phase of International Patent Application No. PCT/NZ2015/050219, filed Dec. 23, 2015, which claims priority to U.S. Provisional Application No. 62/096,469, filed Dec. 23, 2014, which is incorporated herein by reference in its entirety. Any and all applications for which a foreign or domestic priority claim is identified in the Application Data Sheet as filed with the present application are hereby incorporated by reference under 37 C.F.R. § 1.57.

FIELD OF THE DISCLOSURE

The present disclosure relates generally to wound retractors, and more particularly to improvements to wound retractors that may provide for delivery of medical gases to a wound cavity via a diffuser.

BACKGROUND

Surgical procedures, such as open surgery or laparoscopic surgery, for example, colorectal, thoracic, cardiac, obstetrics or gynaecologic surgery, expose tissues of a patient to atmospheric conditions. This may lead to desiccation and evaporative cooling of the wound.

In some instances, gases, for example, carbon dioxide, are used to create a workspace for a surgeon during a laparoscopic surgery. The gases are provided from a gases source, such as an insufflator, that regulates the gases pressure. The gases can be humidified by a humidification apparatus. In open surgery, gases can be used to create a protective space in which the surgeon can work on a wound. Heating and humidification of the gases helps to protect the wound from the harmful effects of cold, dry gases.

In open surgery, a wound retractor provides the surgeon access to the wound by exposing the anatomy on which the procedure is being performed. This creates a cavity in which the surgeon can work. One common type of wound retractor includes a pair of flexible concentric rings with a sleeve spanning there between. The wound retractor can be inserted into the opening of the patient cavity, with the lower ring in contact with the wound. Tension may be applied to the upper ring, for example, by rolling the ring. This causes the sleeve to become taut such that the wound retractor enlarges the wound entry, providing better access for the surgeon. In some instances, wound retractors are self-retaining and, once positioned, require minimal readjustment during the procedure.

Many prior art wound retractors require a user to perform multiple complex steps to insert the retractor into the cavity. Further, different wound geometries may prove difficult to effectively retract. The provision of gases into the cavity requires an additional instrument (in addition to the wound retractor) to be within the cavity. Due to limited space available within the cavity, this may obstruct or inconvenience the surgeon.

SUMMARY

The present disclosure describes wound retractors that can be used to supply gases to a wound during surgical procedures. Embodiments are disclosed wherein the wound retractor includes or is attachable to mechanisms that more accurately and effectively deliver gases to a patient. In an embodiment, the wound retractor provides heated and humidified gases to the wound as a single device. This may reduce the number of components within the workspace of the surgeon. This may also eliminate the step of positioning a separate diffuser within the cavity.

According to at least one aspect of the present disclosure, a diffuser for use with a wound retractor and configured to deliver gases can have one, some, or all of the following features, as well as other features described herein. The diffuser comprises an interface tube. The interface tube comprises a proximal end and a distal end. The distal end is configured to connect to a gases supply. The diffuser comprises a diffuser interface positioned at the proximal end. The diffuser interface is configured for receiving gases from the gases supply through the interface tube. The diffuser interface comprises a diffusion mechanism configured for delivering gases in a diffusion direction.

The interface tube may comprise a branching interface tube. The proximal end of the branching interface tube may comprise a plurality of proximal ends. The diffuser interface may comprise a plurality of diffuser interfaces each positioned at one of the plurality of proximal ends. The diffuser interface may be integrated with the interface tube. The diffuser interface may be attachable to the interface tube. The interface tube may comprise a flexible material. The flexible material may be floppy. The flexible material may be malleable. The interface tube may comprise a rigid material. The diffuser interface may comprise a complete ring shape. The diffuser interface may comprise a partial ring shape. The diffuser interface may branch to one or more outlets.

The diffusion mechanism may comprise one or more perforations formed in the diffuser interface. At least one of the perforations may be configured to provide non-laminar gases flow. At least one of the perforations may be configured to provide laminar gases flow. At least one of the perforations may be any shape, including rectangular or circular. At least one of the perforations may have a linear or curved cross-sectional profile. At least one of the perforations may have a trumpet-shaped cross-sectional profile. The diffusion mechanism may comprise a mesh. The diffusion mechanism may comprise an open cell foam. The diffusion mechanism may comprise a gases permeable membrane. The diffusion direction may be toward a cavity within the wound retractor. The diffusion direction may be inward, toward the center of the cavity. The diffusion direction may be downward, toward the bottom of the cavity. The diffusion direction may be toward a wound edge. The diffusion direction may be omnidirectional.

The diffuser may comprise a coupling mechanism configured to secure the diffuser to the wound retractor. The coupling mechanism may be selectively attachable to the diffuser. The coupling mechanism may be positioned on the interface tube. The coupling mechanism may be positioned on the diffuser interface. The coupling mechanism may comprise a clip. The clip may be biased in the open position (for example, using a spring) or in the closed position (for example, a peg, bulldog, or reverse spring-loaded clip). The clip may be an adjust-and-lock clip (for example, a grub screw with a ball and socket). The coupling mechanism may comprise a malleable member. For example, the malleable member may be a malleable arm configured to wrap around a portion of the wound retractor. The coupling mechanism may comprise an adhesive. The coupling mechanism may be configured to secure the diffuser to the wound retractor via a friction fit.

The wound retractor may comprise an upper ring, a lower ring, and a sleeve extending between and connecting the upper ring and the lower ring, and the coupling mechanism may be configured to secure the diffuser to the wound retractor at the upper ring. The wound retractor may comprise an upper ring, a lower ring, and a sleeve extending between and connecting the upper ring and the lower ring, and the coupling mechanism may be configured to secure the diffuser to the wound retractor at the lower ring. The wound retractor may comprise an upper ring, a lower ring, and a sleeve extending between and connecting the upper ring and the lower ring, and the coupling mechanism may be configured to secure the diffuser to the wound retractor at the sleeve. The wound retractor may comprise a conventional metal retractor, and the coupling mechanism may be configured to secure the diffuser to a portion of the metal retractor. The diffuser may comprise a coupling mechanism configured to secure the diffuser to another surgical instrument.

According to at least one aspect of the present disclosure, a wound retractor can have one, some, or all of the following features, as well as other features described herein. The wound retractor comprises an upper ring. The wound retractor comprises a lower ring. The wound retractor comprises a sleeve extending between and connecting the upper ring to the lower ring. The wound retractor comprises a diffuser interface. The diffuser interface comprises a gases inlet and a diffusion mechanism.

The wound retractor may comprise an interface tube. The interface tube may comprise a distal end configured to connect to a gases supply. The interface tube may comprise a proximal end configured to connect to the gases inlet. The interface tube may comprise a branching interface tube. The proximal end of the branching interface tube may comprise a plurality of proximal ends. The diffuser interface may comprise a plurality of diffuser interfaces each positioned at one of the plurality of proximal ends. The diffuser interface may be integrated with the interface tube. The diffuser interface may be attachable to the interface tube. The interface tube may comprise a flexible material. The flexible material may be floppy. The flexible material may be malleable. The interface tube may comprise a rigid material. The gases inlet may be positioned on the upper ring. The gases inlet may be positioned on the lower ring. The gases inlet may be positioned on the sleeve.

The diffuser interface may be integrated with the upper ring. The upper ring may comprise a hollow gases channel and the diffusion mechanism may be integrated into the upper ring. The diffuser interface may be integrated with the lower ring. The lower ring may comprise a hollow gases channel and the diffusion mechanism may be integrated into the lower ring. The diffuser interface may be integrated with the sleeve. The sleeve may comprise an inner layer and an outer layer separated by a space. At least one of the inner layer or the outer layer may be configured to be at least partially removable. The diffuser interface may comprise a spiral conduit attached to the sleeve. The spiral conduit may be attached to an inner surface of the sleeve. The diffuser interface may comprise one or more ribs attached to an outer surface of the sleeve. The ribs may be configured to define gases channels between the outer surface of the sleeve and a wound edge in use.

The diffusion mechanism may comprise one or more perforations formed in the diffuser interface. At least one of the perforations may be configured to provide non-laminar gases flow. At least one of the perforations may be configured to provide laminar gases flow. The diffusion mechanism may comprise a mesh. The diffusion mechanism may comprise an open cell foam. The diffusion mechanism may comprise a gases permeable membrane. The sleeve may be gases permeable.

The wound retractor may comprise a gases pathway within the diffuser interface. The gases pathway may comprise a directly plumbed pneumatic connection with at least one of the upper ring, the lower ring, or a pocket formed within the sleeve. The gases pathway may comprise a pocket formed between an inner layer of the sleeve and an outer layer of the sleeve. The pocket may connect a gases channel in the upper ring with a gases channel in the lower ring. The gases pathway may comprise one or more tubes extending between the upper ring and the lower ring. At least one of the tubes may be adjacent to an inner surface of the sleeve. At least one of the tubes may be adjacent to an outer surface of the sleeve. The gases pathway may comprise a porous material. The porous material may comprise a foamed or a sintered material.

The wound retractor may comprise one or more valves configured to control gases flow from the diffuser interface. At least one of the valves may be manually controllable. The wound retractor may comprise one or more gases flow rate sensors. At least one of the valves may be automatically controllable based at least in part on data received from the gases flow rate sensors.

According to at least one aspect of the present disclosure, a wound retractor can have one, some, or all of the following features, as well as other features described herein. The wound retractor comprises an upper ring, a lower ring, and a sleeve extending between and connecting the lower ring to the upper ring, wherein the sleeve is gases permeable.

The sleeve may comprise a gases permeable material. The sleeve may comprise perforations configured to allow gases to pass through. The wound retractor may comprise a sleeve extender. The sleeve extender may extend above the wound retractor. The sleeve extender may increase the depth of a cavity within the wound retractor. The sleeve extender may be permeable to gases. The sleeve extender may be impermeable to gases. The sleeve extender may be attachable to the upper ring. The sleeve extender may be attachable to the lower ring. The sleeve extender may be attachable to the sleeve.

The sleeve may be configured to direct gases flow. The sleeve may comprise an absorbent material. The absorbent material may be positioned on an outer layer of the sleeve. The absorbent material may be positioned on an inner layer of the sleeve. The absorbent material may be configured to absorb water, a medicament, or a therapeutic liquid. The absorbent material may comprise a chemical configured to produce an exothermic reaction when wetted. The wound retractor may comprise an ampule. The ampule may be configured to hold water, a medicament, or a therapeutic liquid. The ampule may be attached to the upper ring, the lower ring, or the sleeve. The sleeve may comprise an inner layer and an outer layer separated by a space. At least one of the inner layer and the outer layer may be configured to be at least partially removable. The wound retractor may comprise a volume of foam attached to an outer surface of the sleeve.

At least one of the upper ring and the lower ring may be configured to go through a transformation between a larger diameter state and a smaller diameter state. The transformation may be actuated by application of an electrical current.

The transformation may be actuated by application of pneumatic pressure. The transformation may be actuated by a mechanical feature of the upper ring and/or the lower ring. The mechanical feature may be a tethered coil or spring, mechanical iris, or expandable truss. The sleeve may comprise a zipper.

For purposes of summarizing the disclosed systems and apparatus, certain aspects, advantages, and novel features of the disclosed systems and apparatus have been described herein. It is to be understood that not necessarily all such advantages may be achieved in accordance with any particular embodiment of the disclosed systems and apparatus. Thus, the disclosed systems and apparatus may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects, and advantages of the present disclosure will be described with respect to the following figures, which are intended to illustrate and not to limit the preferred embodiments. In the figures, similar elements have similar reference numerals.

DETAILED DESCRIPTION

Figure 1A:
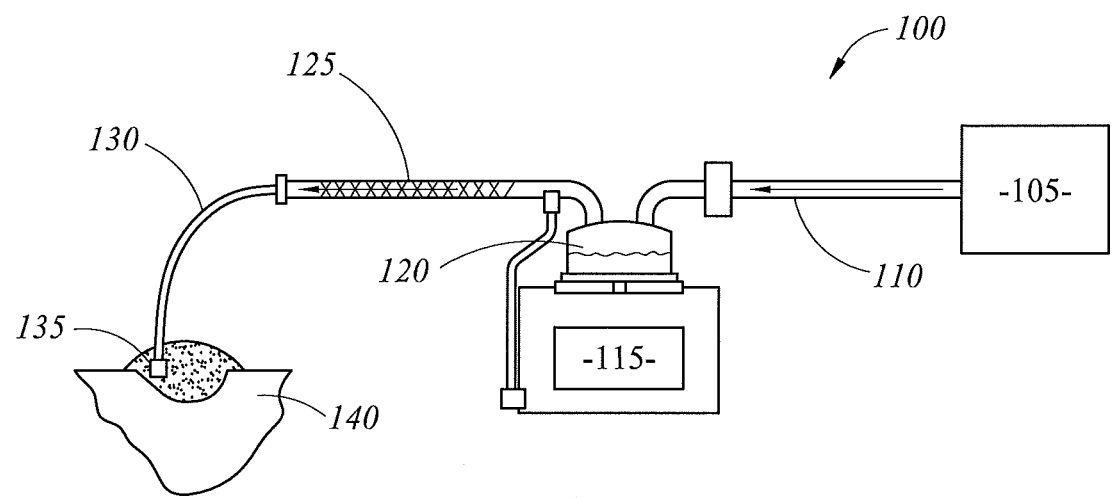
FIG. 1A illustrates a schematic view of a gases delivery system for use during a surgical procedure according to an embodiment of the present disclosure.

The following description is merely illustrative in nature and is in no way intended to limit the scope of the present disclosure or its application or uses. For purposes of clarity, the same or similar reference numbers will be used in the drawings to identify similar elements. However, for the sake of convenience, certain features present or annotated with reference numerals in some figures of the present disclosure are not shown or annotated with reference numerals in other figures of the present disclosure. Unless the context clearly requires otherwise, these omissions should not be interpreted to mean that features omitted from the drawings of one figure could not be equally incorporated or implemented in the configurations of the disclosed methods, apparatus and systems related to or embodied in other figures. Conversely, unless the context clearly requires otherwise, it should not be assumed that the presence of certain features in some figures of the present disclosure means that the disclosed methods, apparatus and systems related to or embodied in such figures must necessarily include these features.

It is to be understood that the systems and apparatus disclosed herein can exist in any combination or permutations. Thus, features from different embodiments can be synergistically combined without departing from the scope of the disclosed apparatus and systems.

FIG. 1A illustrates a schematic view of a gases delivery system 100 for use during a surgical procedure according to an embodiment of the present disclosure. The surgical procedure could be either laparoscopic or open surgery. The gases delivery system 100 includes a gases source 105, a gases supply tube 110, a humidification apparatus 115, a delivery tube 125, an interface tube 130, and an interface 135. The humidification apparatus 115 includes a humidification chamber 120. Gases from the gases source 105 travel through the gases supply tube 110 to the humidification apparatus 115 where they are heated and humidified. The gases are then delivered to a patient 140 via the delivery tube 125, the interface tube 130, and the interface 135, respectively. The term "gases" is used herein broadly to refer to any gas and/or combination of gases that may be used in surgical applications, such as, carbon dioxide, helium, air, carbon dioxide combined with nitrous, carbon dioxide combined with oxygen, among others. Other gases and combinations also fall within the scope of the present disclosure. In an embodiment, the delivery tube 125 and the interface tube 130 comprise a single tube that delivers the humidified gases to the interface 135. In an embodiment, a single component integrates the delivery tube 125, the interface tube 130, and the interface 135.

Figure 1B:
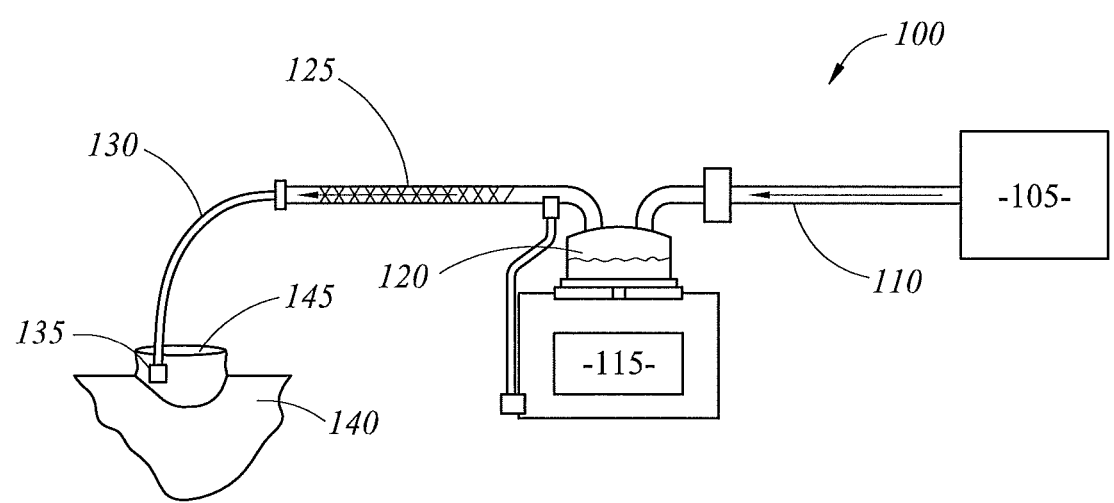
FIG. 1B illustrates a schematic view of the gases delivery system of FIG. 1A used with a wound retractor according to an embodiment of the present disclosure.

FIG. 1B illustrates a schematic view of the gases delivery system 100 used with a wound retractor 145 according to an embodiment of the present disclosure. The wound retractor 145 may be used to increase the workspace of the surgeon, increase accessibility to the wound, improve visualisation of the wound, and reduce trauma to the patient 140 during the procedure, among other purposes.

In an embodiment, the humidification apparatus 115 generates humidity via a mechanism other than pass-over humidification, such as, for example, a heated absorbent material that holds water. Thus, the humidification apparatus 115 can be a compact component and easily integrated into the system. In an embodiment, the humidification apparatus 115 may be integral to the delivery tube 125 and/or the interface tube 130. In an embodiment, the humidification apparatus 115 is configured to be in-line with the delivery tube 125 and/or the interface tube 130. This may allow the humidification apparatus 115 to be proximal to the patient 140.

Figure 2A:
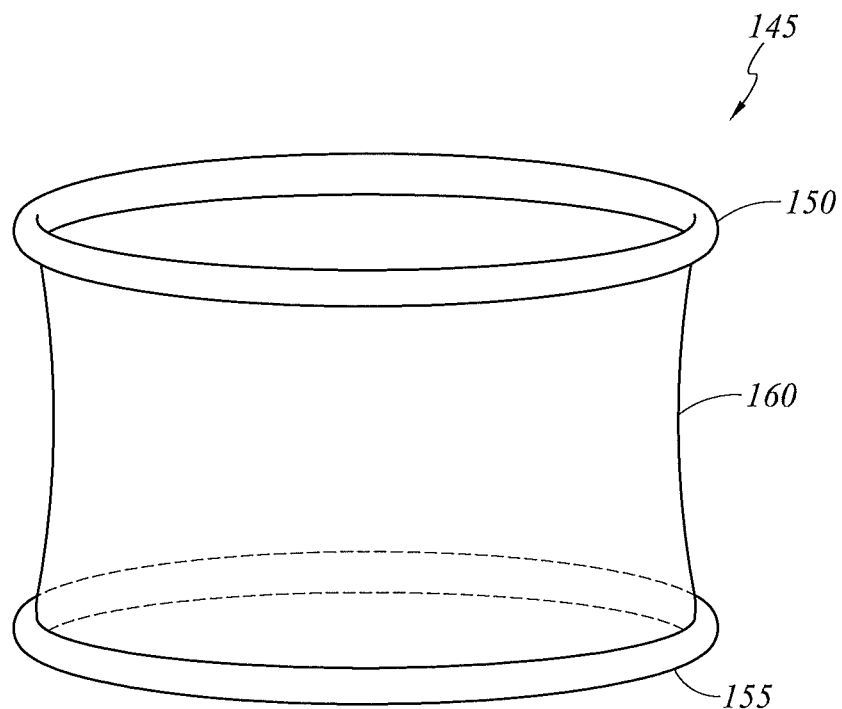
FIGS. 2A and 2B illustrate various views of a wound retractor according to embodiments of the present disclosure.
Figure 2B:
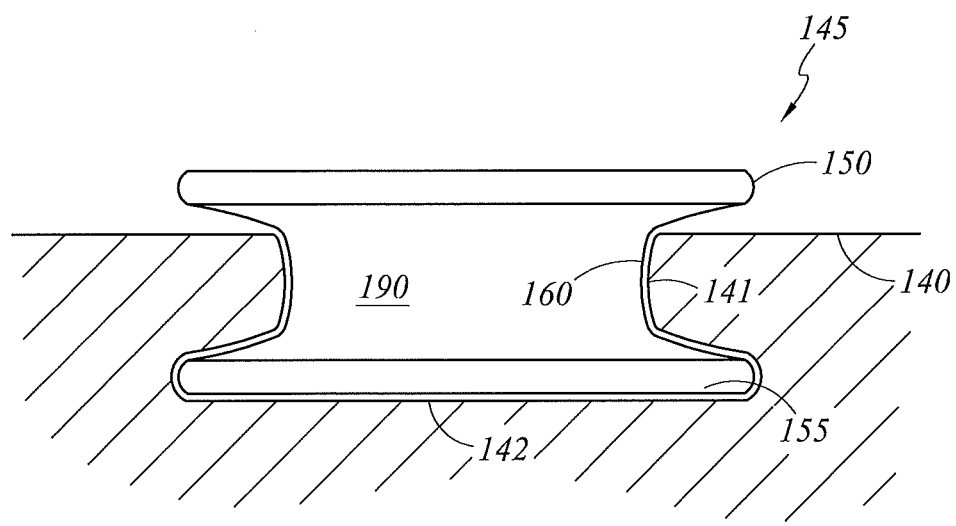

FIG. 2A illustrates a perspective view of the wound retractor 145, and FIG. 2B illustrates a cross-sectional view of the wound retractor 145 in use, according to embodiments of the present disclosure. In an embodiment, the wound retractor 145 comprises an upper ring 150, a lower ring 155, and a sleeve 160 extending between and connecting the upper ring 150 and the lower ring 155. The sleeve 160 may comprise a flexible material, such as a film, that may be permeable or impermeable to liquids and/or gases. The sleeve 160 may be robust so as to reduce or eliminate the likelihood of tears or punctures. In an embodiment, the sleeve 160 is at least partially transparent. In an embodiment, the sleeve 160 is opaque.

As illustrated in FIG. 2B, in use on the body of the patient 140 during a procedure, the sleeve 160 seals against a wound edge 141. The sleeve 160 is configured to retract the wound edge 141 and to prevent exposure of the wound edge 141 to bacteria. The seal may also isolate the wound edge 141 from exposure to gases delivered to the wound 142 during the procedure. The wound edge 141, as described herein, is a part of the wound 142 that sits against an outer layer of the sleeve 160, and thus, is located around the perimeter of the area enclosed by the wound retractor 145. The wound 142, as described herein, refers to the tissue that lies within the wound retractor 145 when the wound retractor 145 is inserted into the patient 140. The wound retractor 145 forms a cavity 190, which, as described herein, refers to the area created by the wound retractor 145 that provides access to the wound 142. With the wound retractor 145 in place, the wound 142 is accessible through the opening in the upper ring 150 and the cavity 190.

To insert the wound retractor 145 into the patient 140, the lower ring 155 is inserted into an incision such that it is adjacent to the wound 142. The upper ring 150 is then positioned above the wound 142. Tension may be applied to the sleeve 160, for example, by rotating or rolling the upper ring 150, causing the sleeve 160 to fit snugly against the wound edge 141, thus creating the cavity 190 within the wound retractor 145. The upper ring 150 and the lower ring 155 can be made from a flexible plastic material. The upper ring 150 and the lower ring 155 may be manipulated into place adjacent to the wound 142, for example by compression, but expand to their original shapes following insertion.

As discussed above, the sleeve 160 of the wound retractor 145 seals against the wound edge 141. In an embodiment, the sleeve 160 comprises a gases impermeable material that isolates the wound edge 141 from exposure to gases delivered to the cavity 190 (for example, using the gases delivery system 100). In an embodiment, the sleeve 160 comprises a gases permeable material that exposes the wound edge 141 to gases delivered to the cavity 190. In some embodiments, gases delivered to the cavity 190 may have a beneficial effect when exposed to the wound edge 141.

Gases such as carbon dioxide have been shown to have a beneficial effect, known as the Bohr Effect, when in contact with body tissue. The Bohr Effect occurs due to an increased partial pressure of carbon dioxide in the blood, which causes the blood pH to decrease. As a result, oxygen is less tightly bound to the haemoglobin within the erythrocytes. Thus, an increased exposure of tissue to carbon dioxide increases oxygen release within the tissue. This increases the speed of wound healing and reduces the risk of surgical site infection and post-operative pain.

In an embodiment, other gases or combinations of gases provide beneficial effects to body tissue. For example, but without limitation: a combination of carbon dioxide and nitrous provides a local anaesthetic effect when in contact with tissue; a combination of carbon dioxide and oxygen further increases tissue oxygenation; and helium reduces tissue acidosis. It is to be understood that use of these gases, or other gases not listed above also fall within the scope of the disclosed apparatus and systems.

Figure 3A:
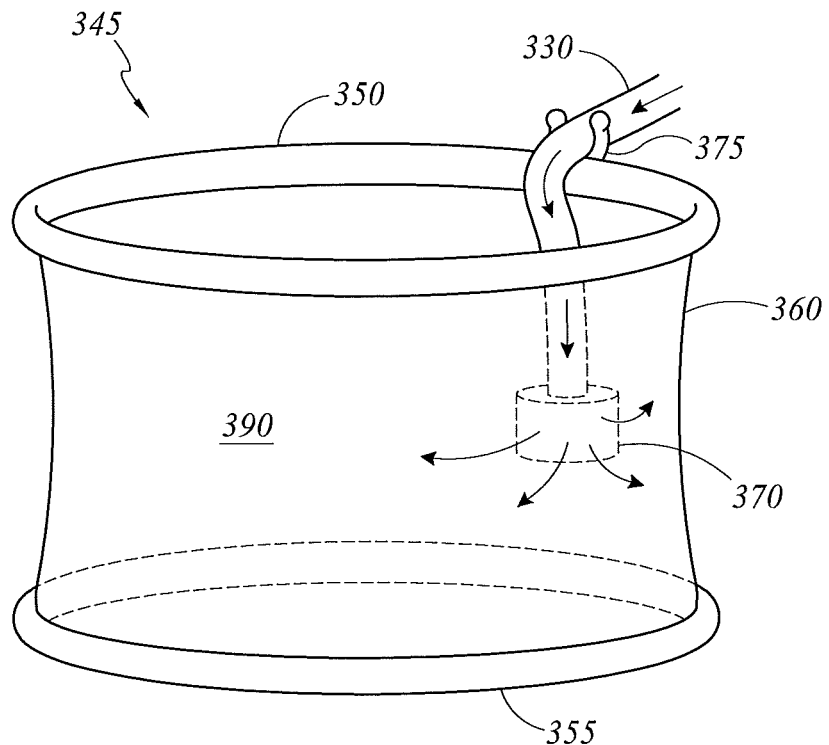
FIGS. 3A and 3B illustrate perspective views of a wound retractor including features for clipping a diffuser onto the wound retractor according to embodiments of the present disclosure.
Figure 3B:
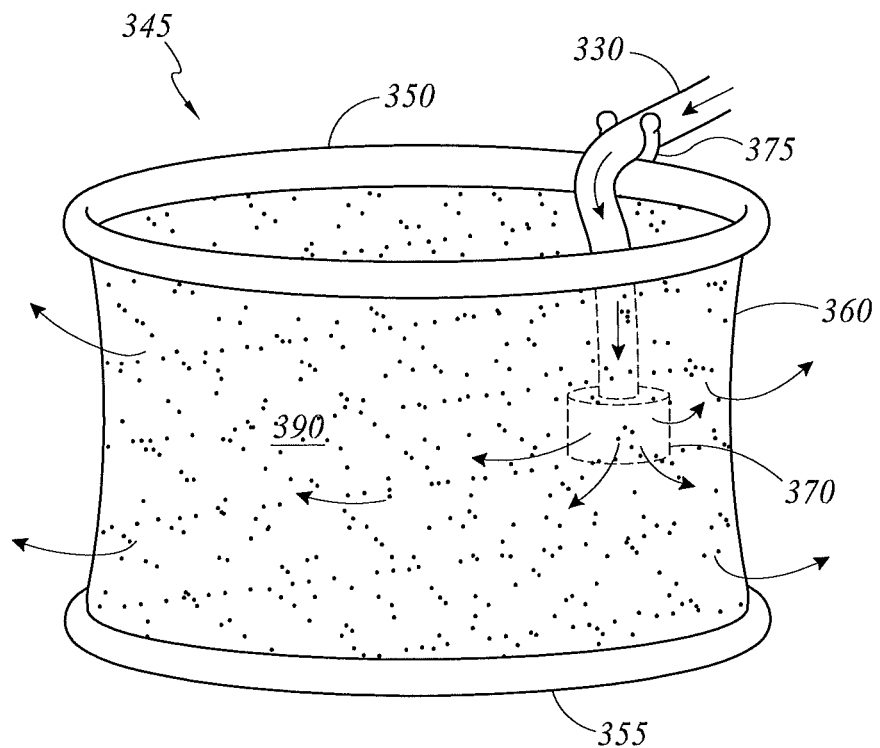

FIGS. 3A and 3B illustrate perspective views of a wound retractor 345 including features for clipping a diffuser 370 onto the wound retractor 345 according to embodiments of the present disclosure. In an embodiment, the diffuser 370 is a conventional diffuser. The wound retractor 345 includes an upper ring 350, a lower ring 355, and a sleeve 360 extending between and connecting the upper ring 350 and the lower ring 355 and creating a cavity 390 in use. In the illustrated embodiment, a coupling mechanism 375 is attached to the upper ring 350. The coupling mechanism 375 may be a compliant or mechanical clip, or other suitable structure. The coupling mechanism 375 is configured to secure an interface tube 330 and/or the diffuser 370 to the upper ring 350, thus holding the diffuser 370 in position during a procedure. In an embodiment, the diffuser 370 is secured in position so as to be located within the cavity 390. In an embodiment, the diffuser 370 is positioned proximate the sidewall of the sleeve 360. Thus, the diffuser 370 delivers gases to the cavity 390. The wound retractor 345 including a coupling mechanism 375 may reduce frustration of a surgeon caused by a loose or unsecured diffuser positioned within the limited workspace.

In an embodiment, the coupling mechanism 375 may be integrally molded with the upper ring 350. In an embodiment, the coupling mechanism 375 may comprise a separate part that is attached to the upper ring 350. For example, the coupling mechanism 375 may be attached with adhesives or snap-fit onto the upper ring 350. Thus, the coupling mechanism 375 may be permanently or removably attached to the upper ring 350. The coupling mechanism 375 may be a rigid or compliant part that receives the interface tube 330 and/or the attached diffuser 370. In an embodiment, the coupling mechanism 375 comprises prong-like structures that are configured to flex to allow insertion and securement of the interface tube 330 and/or the attached diffuser 370.

Although described above, and illustrated in the figures, as attached to the upper ring 350, in an embodiment, the coupling mechanism 375 may be attached to the lower ring 355 or to the sleeve 360. In an embodiment, the coupling mechanism 375 may comprise multiple coupling mechanisms, and the upper ring 350 and the lower ring 355 may each include one or more of the coupling mechanisms 375.

In the embodiment illustrated in FIG. 3A, the sleeve 360 is formed from a material that is impermeable to gases. Thus, gases diffusing from the diffuser 370 are generally contained within the cavity 390. In the embodiment illustrated in FIG. 3B, the sleeve 360 is formed from a material that is permeable to gases. For example, the sleeve 360 may be perforated with holes or comprise a gases permeable mesh or other gases permeable material. Thus, gases diffusing from the diffuser 370 into the cavity 390 can pass through the sleeve 360 to the wound edge 141. As a result, the wound edge 141 benefits from the heated, humidified gases.

Figure 4A:
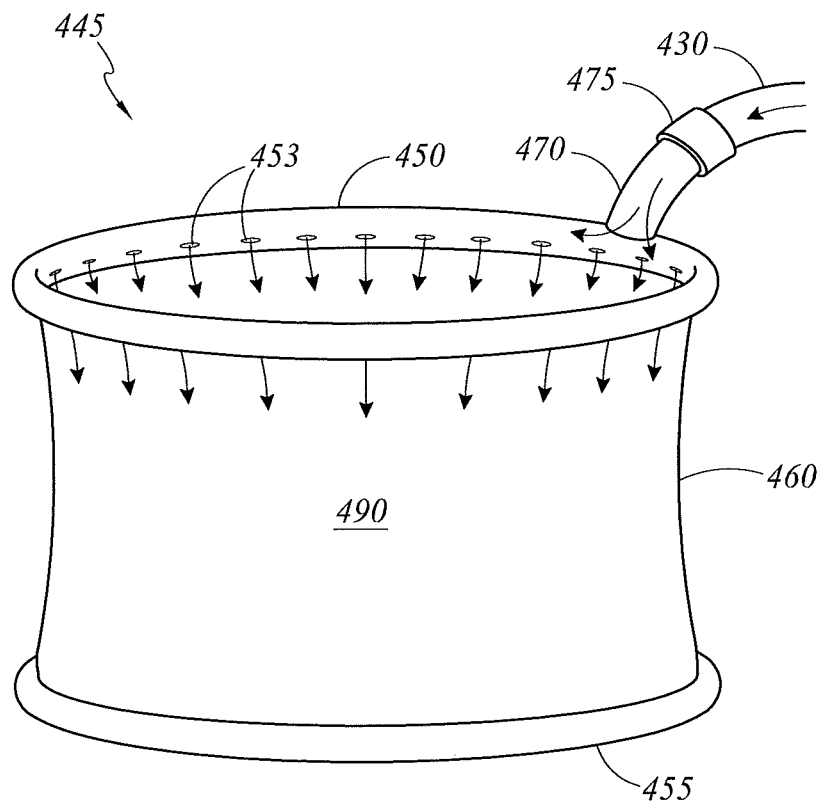
FIGS. 4A through 4C illustrate various views of a wound retractor including a diffusing upper ring according to embodiments of the present disclosure.
Figure 4B:
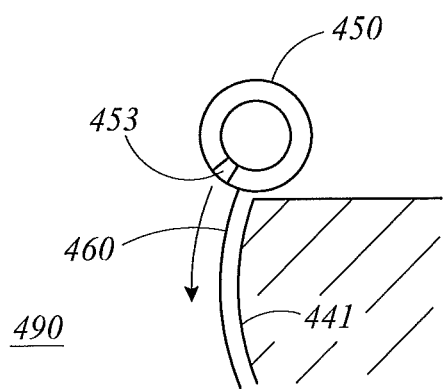
Figure 4C:
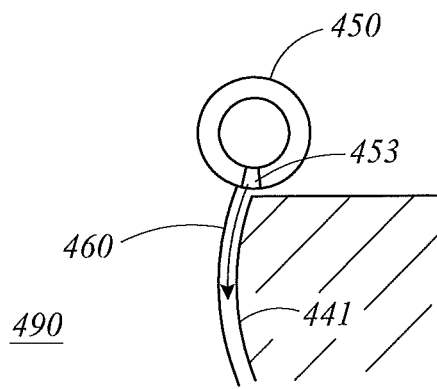

FIGS. 4A through 4C illustrate various views of a wound retractor 445 including a diffusing upper ring 450 according to embodiments of the present disclosure. FIG. 4A illustrates a perspective view of the wound retractor 445 including the diffusing upper ring 450, a lower ring 455, and a sleeve 460 extending between and connecting the diffusing upper ring 450 and the lower ring 455 and creating a cavity 490 in use. The diffusing upper ring 450 may be hollow, defining a flow path for gases therein. The diffusing upper ring 450 may include a gases inlet 470. The gases inlet 470 may be connectable to an interface tube 430 for receiving gases from a gases source. The gases inlet 470 may include a connector 475 for connecting to the interface tube 430.

The diffusing upper ring 450 may include one or more perforations 453 along a lower surface of the diffusing upper ring 450. The perforations 453 may be configured to direct gases into the cavity 490 and toward the wound. The perforations 453 may be directed openings. FIG. 4B illustrates a partial cross-sectional view of the diffusing upper ring 450 according to an embodiment of the present disclosure, where the perforations 453 are configured to direct gases along an inner wall of the sleeve 460 and into the cavity 490. FIG. 4C illustrates a partial cross-sectional view of the diffusing upper ring 450 according to an embodiment of the present disclosure, where the perforations 453 are configured to direct gases along an outer wall of the sleeve 460, between the sleeve 460 and the wound edge 441. In an embodiment, the gases may be directed downward. In an embodiment, the gases may be directed across the opening of the cavity 490, at least in part to create an air curtain effect. Such a configuration may reduce or prevent contaminants, such as bacteria, from reaching or settling on the wound or the wound edge 441. In an embodiment, the sleeve 460 is gases permeable such that the gases are also delivered through the sleeve 460 to the wound edge 441.

Although the embodiments disclosed herein have been described in reference to the upper ring 450, in an embodiment, the perforations and gases inlet may be included on the lower ring 455 instead of or in addition to the upper ring 450.

Figure 5A:
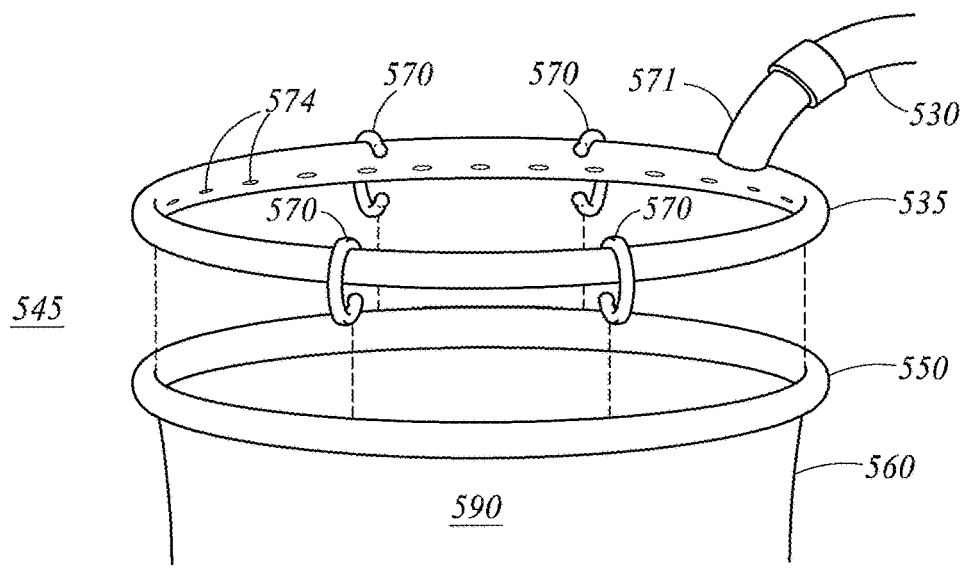
FIGS. 5A through 5C illustrate various views of a wound retractor including a ring-shaped diffuser interface that can be clipped onto a ring of the wound retractor according to embodiments of the present disclosure.
Figure 5B:
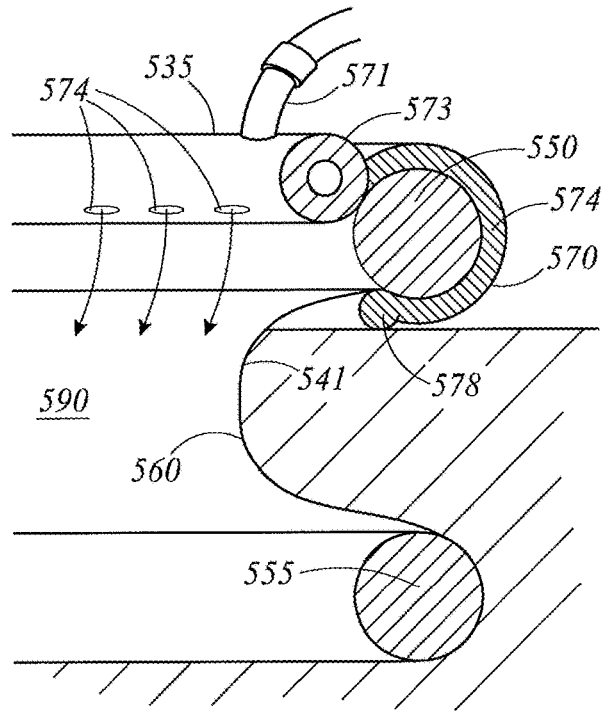
Figure 5C:
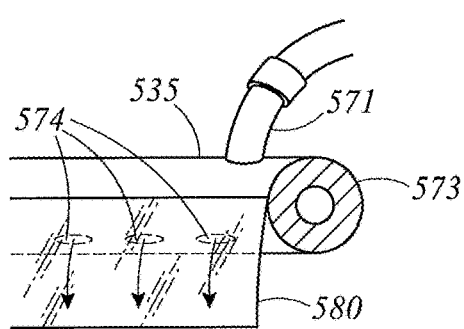

FIGS. 5A through 5C illustrate various views of a wound retractor 545 including a ring-shaped diffuser interface 535 that can be clipped onto a ring of the wound retractor 545 according to embodiments of the present disclosure. FIG. 5A illustrates an exploded partial perspective view of the wound retractor 545. The wound retractor 545 includes an upper ring 550, a lower ring 555, and a sleeve 560 extending between and connecting the upper ring 550 and the lower ring 555. The diffuser interface 535 may include one or more coupling mechanisms 570 that are configured to attach the diffuser interface 535 to the upper ring 550. In an embodiment, the coupling mechanisms 570 extend at least partially around the perimeter of the upper ring 550. In an embodiment, the coupling mechanisms 570 extend fully around the perimeter of the upper ring 550. In an embodiment, the coupling mechanisms 570 comprise one or more discrete clips that are used to couple the diffuser interface 535 to the upper ring 550 at several locations. In an embodiment, the coupling mechanisms 570 clip onto the outside of the upper ring 550. In an embodiment, the coupling mechanisms 570 are reversibly clipped onto the outside of the upper ring 550. The coupling mechanisms 570 can be attached to, for example, the wound retractor 145, as well as other wound retractors. In an embodiment, the coupling mechanisms 570 and the diffuser interface 535 are separate pieces, while, in other embodiments, they are integrally formed.

FIG. 5B illustrates a partial cross-sectional view of the wound retractor 545 and the diffuser interface 535, where one of the coupling mechanisms 570 may include a clip 574 that is attached (either permanently or removably) to a surface of the diffuser interface 535. In an embodiment, the clip 574 is attached to the diffuser interface 535 at a lower surface of the diffuser interface 535. In an embodiment, the clip 574 is attached to the diffuser interface 535 at a side surface of the diffuser interface 535. In an embodiment, the clip 574 is attached to the diffuser interface 535 at an upper surface of the diffuser interface 535. In an embodiment, the clip 574 extends around the outside of the upper ring 550. A hook 578 is formed at the end of the clip 574 and helps to secure the clip 574 onto the upper ring 550. The sleeve 560 extends from the base of the upper ring 550, over the top of the hook 578, and to the lower ring 555.

The diffuser interface 535 may comprise a gases permeable material that enables gases to diffuse into the cavity. In an embodiment, the diffuser interface 535 comprises directed openings 574. The directed openings 574 as described herein refer to perforations designed to direct the flow of gases. For example, the directed openings 574 may comprise openings, channels, or holes with specific shapes. The shapes may be designed to reduce the velocity of the gases. The gases permeable material comprising perforations may be a plastics material. In an embodiment, the material may be a semi-rigid or rigid plastics material. The directed openings 574 can be present around the entire perimeter of the diffuser interface 535 or only in certain locations on the diffuser interface 535. In an embodiment, the gases permeable material of the diffuser interface 535 comprises a foam material or an open cell foam material.

The diffuser interface 535 may comprise a ring; that is, the diffuser interface 535 may be ring-shaped. The diffuser interface 535 may comprise a tube 573 with a hollow cross-section, as illustrated in FIG. 5B. A gases inlet 571 connects with an interface tube 530 to allow gases to enter the tube 573. The gases are then diffused into the cavity via the gases permeable material of the diffuser interface 535 or the directed openings 574. In an embodiment, the diffuser interface 535 may comprise an impermeable side, cover, or film to prevent or reduce the likelihood of gases diffusing into the wound edge. In an embodiment, the entirety of the diffuser interface 535 is gases permeable such that gases diffuse into the cavity through the sleeve 560 to the wound edge. In an embodiment, the diffuser interface 535 may not comprise a full ring shape; that is, the diffuser interface 535 may comprise only an arcuate shape that extends partially around the upper ring 550.

FIG. 5B illustrates a partial cross-sectional view of the wound retractor 545 and the diffuser interface 535. The diffuser interface 535 comprises a bifurcating structure, or a structure with multiple gases entry points. In an embodiment, the diffuser interface 535 comprises a foamed material or an open cell foam material. In an embodiment, the diffuser interface 535 comprises directed openings. In an embodiment, the diffuser interface 535 comprises perforations to provide gases to the cavity. The perforations may alter in size, such that larger perforations are proximal the wound. This improves diffusion of the gases to the wound through the perforations and maintains a more consistent flow rate along the length of the sleeve 560. The bifurcating structure allows at least a part of the diffuser interface 535 to be positioned within the cavity, for example, tucked beneath the skin of the patient and out of the way of the surgeon. Thus, the diffuser interface 535 is less obtrusive during the procedure. The surgeon can arrange the position of the diffuser interface 535 within the cavity.

The diffuser interface 535 has a large area in which to diffuse the gases to the cavity. In an embodiment, the diffuser interface 535 comprises different shapes, such as, for example, a flat diffuser. In an embodiment, the diffuser interface 535 comprises a memory such that the diffuser interface 535 can maintain its manipulated shape. The diffuser interface 535 pneumatically connects with the interface tube 530.

In an embodiment, the sleeve 560 is impermeable to gases flow. In an embodiment, the sleeve 560 is permeable to gases flow such that gases diffuse into both the cavity and the wound edge.

In an embodiment, the diffuser interface 535 couples with the upper ring 550. The coupling mechanism 570 couples the diffuser interface 535 with the upper ring 550. In an alternative, adhesives or welding can couple the diffuser interface 535 with the upper ring 550. The diffuser interface 535 is configured to be a separate component to the wound retractor 545. Thus, in an embodiment, the diffuser interface 535 is configured to couple with, for example, the wound retractor 145 or other wound retractors.

In an embodiment, the lower ring 555 comprises a clip or additional coupling mechanism to couple with the diffuser interface 535. The clip or additional coupling mechanism may be used in addition to the coupling mechanism 570, or instead of the coupling mechanism 570. In an embodiment, the coupling mechanism 570 is positioned to couple the diffuser interface 535 with the lower ring 555.

In an embodiment, the diffuser interface 535 is configured to be positioned outside the cavity. The diffuser interface 535 is manipulated to fit between the wound edge and the wound retractor 545. This reduces obstruction to the surgeon during the procedure. Also, the wound edge receives heated and humidified gases from the diffuser interface 535. The sleeve 560 comprises a gases permeable material such that gases diffuse through the sleeve 560 into the cavity.

FIG. 5C illustrates a partial cross-sectional view of the diffuser interface 535 with a sheet 580 bonded to the diffuser interface 535 so that gases directed out of the openings 574 travel down between the wound edge and the sheet 580 and exit into the wound at the base of the sheet 580. The sheet 580 may have ridges on the interior surface to form channels for gases to travel down between the sheet 580 and the wound edge. This embodiment may be used with retractors that do not have integrated sleeves, such as old style metal retractors.

Although the wound retractor 545 has been described above with reference to the diffuser interface 535 clipping to the upper ring 550, in an embodiment, the diffuser interface 535 may be clipped to the lower ring 560 in the same manner.

Figure 6A:
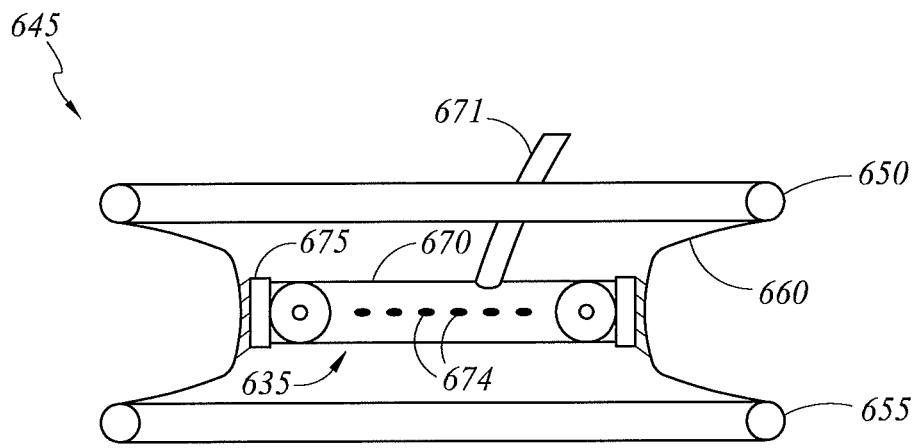
FIGS. 6A through 6D illustrate various views of a wound retractor including a diffuser interface that is attachable to the wound retractor according to embodiments of the present disclosure.
Figure 6B:
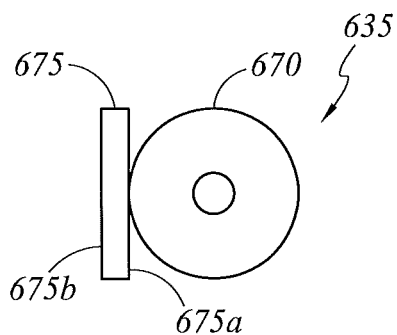
Figure 6C:
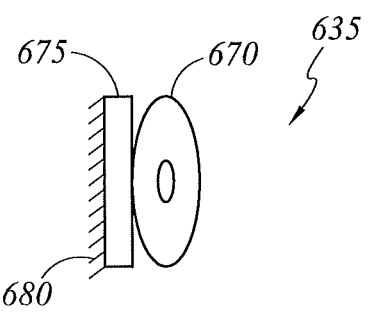
Figure 6D:
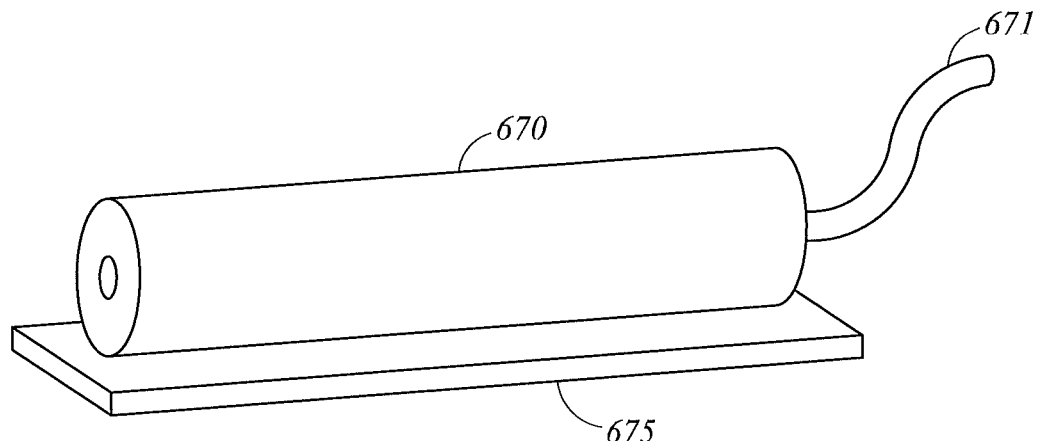

FIG. 6A illustrates a cross-sectional view of an embodiment of a wound retractor 645 with an embodiment of a diffuser interface 635 that is attachable to a sleeve 660. The wound retractor 645 includes an upper ring 650, a lower ring 655, and the sleeve 660 extending between and connecting the upper ring 650 and the lower ring 655. FIGS. 6B through 6D illustrate additional views of the diffuser interface 635 of FIG. 6A.

The diffuser interface 635 is configured to couple with the sleeve 660 to provide gases to the cavity. In the illustrated embodiment, the diffuser interface 635 comprises a tube 670 and a coupling member 675. The coupling member 675 is configured to attach (either permanently or removably) to the sleeve 660 as described below. In an embodiment, the coupling member 675 is configured to be made from sprung steel. In an embodiment, the coupling member 675 is configured to be made from a flexible plastics material. The tube 670 is configured to be permeable to gases. In an embodiment, the tube 670 includes directed openings 674 or perforations.

As illustrated in FIG. 6B, a first surface 675a of the coupling member 675 is configured to couple to the tube 670. A second surface 675b of the coupling member 675 is configured to couple with the sleeve 660. The coupling member 675 may couple with the tube 670 via adhesives, clipping mechanisms, welding, or other suitable method. In an embodiment, the coupling member 675 is permanently coupled with the tube 670. In an embodiment, the coupling member 675 removably couples with the sleeve 660 via adhesives or a clipping mechanism. In an embodiment, the coupling member 675 is integrated into the sleeve 660. In an embodiment, the coupling member 675 is permanently coupled with the sleeve 660, such as, for example, by a snap-fit mechanism, adhesives or welding.

In an embodiment, the coupling member 675 comprises a grip 680, as illustrated in FIG. 6C. In an embodiment, the grip 680 is a rubberized grip. The grip 680 may provide a surface able to be grasped by a user during setup or installation of the diffuser interface 635. In an embodiment, the grip 680 provides a roughened surface that facilitates better coupling between the coupling member 675 and the sleeve 660. In an embodiment, the grip 680 increases the friction between the coupling member 675 and the sleeve 660.

In an embodiment, the diffuser interface 635 is integral to the wound retractor 645. In an embodiment, the diffuser interface 635 is a separate part that is removably or permanently coupled with the wound retractor 645. The diffuser interface 635 may be configured to couple with the wound retractor 645 prior to or after insertion of the wound retractor 645 into the cavity. In an embodiment, tension is applied to the diffuser interface 635 to facilitate insertion of the wound retractor 645 into the cavity. Tension may, for example, reduce the size of the diffuser interface 635 during insertion. FIG. 6C illustrates the diffuser interface 635 in a contracted state while under tension. Removal of the tension allows the diffuser interface 635 to expand. FIG. 6B illustrates the diffuser interface 635 in an expanded state once the tension has been removed. Expansion causes the diffuser interface 635 to be positioned proximal to the wound.

In an embodiment, the diffuser interface 635 presses into the wound. This may allow for localized diffusion of gases to the wound. In an embodiment, the diffuser interface 635 is configured to couple with, for example, the sleeve 160 of the wound retractor 145. Thus, the diffuser interface 635 may be a modular part that is used to adapt the wound retraction systems.

As mentioned above, the coupling member 675 is configured to couple the tube 670 to the sleeve 660. In an embodiment, the coupling member 675 couples the tube 670 to an inner surface of the sleeve 660 (as illustrated in FIG. 6A). In an embodiment, the sleeve 660 is made from a gases permeable material or comprises a gases outlet to facilitate gases movement from inside the cavity to the wound edge. In an embodiment, the gases outlet comprises a valve that controls gases movement to the wound edge. In an embodiment, the sleeve 660 is made from a gases impermeable material and the gases are generally contained within the cavity.

In an embodiment, the coupling member 675 couples the tube 670 to an outer surface of the sleeve 660. In an embodiment, the sleeve 660 may comprise a gases permeable material to allow gases to diffuse into the cavity. In an embodiment, the sleeve 660 may comprise a gases inlet such that gases can enter the cavity. In an embodiment, the gases inlet comprises a valve to control the gases flow into the cavity. Thus, both the wound edge and the cavity receive heated, humidified gases.

The tube 670 may comprise a gases permeable material, for example, a foam or an open cell foam such that gases diffuse through the tube into the cavity or wound edge, or may be made from a gases impermeable material and include directed openings 674 or perforations. The diffuser interface 635 may be configured to wrap at least partially around a surface of the sleeve 660. In an embodiment, the diffuser interface 635 is configured to wrap around the full perimeter of the sleeve 660. In an embodiment, multiple diffuser interfaces 635 are used to deliver gases and may be positioned on multiple locations on the sleeve 660. Thus, delivery of gases may target specific areas of the cavity or may be used to provide additional gases to the cavity or the wound edge. In an embodiment, at least one diffuser interface 635 is positioned on both the inner and outer surface of the sleeve 660. Thus, the wound edge and the cavity are sufficiently provided with gases throughout the procedure. In an embodiment, the tube 670 may not comprise a fully enclosed wall, but a partial wall. For example, the tube 670 may be helical in shape or may resemble a horseshoe.

The diffuser interface 635 may include a gases inlet 671 that couples the diffuser interface 635 to a gases source (not shown). The gases inlet 671 may connect to a side of the tube 670 (as illustrated in FIG. 6A) or an end of the tube 670 (as illustrated in FIG. 6D). In an embodiment, a connector may facilitate coupling between the gases inlet 671 and an interface tube (not shown) which is connected to the gases source. In an embodiment where multiple diffuser interfaces 635 are used, a single interface tube may be bifurcated such that each of the gases inlets 671 of the multiple diffuser interfaces 635 are supplied with gases from the gases source. The interface tube and/or gases inlets may be configured to be a highly flexible.

Although the diffuser interface 635 has been described as attaching to the sleeve 660, in an embodiment, the diffuser interface 635 may be configured to attach to the upper ring 650 and/or the lower ring 655.

Figure 7:
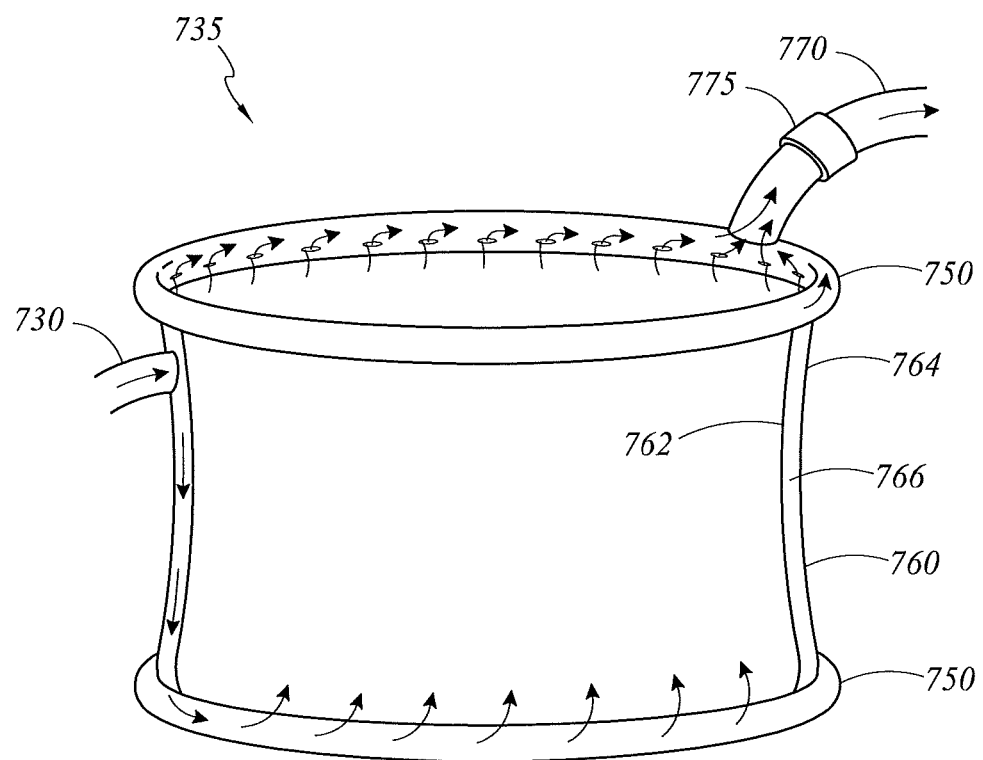
FIG. 7 illustrates a perspective view of a wound retractor configured for scavenging smoke or gases from a cavity according to an embodiment of the present disclosure.

FIG. 7 illustrates a perspective view of a wound retractor 735 configured for scavenging smoke or gases from the cavity according to an embodiment of the present disclosure. The wound retractor 735 comprises an upper ring 750, a lower ring 755 and a sleeve 760 extending between and connecting the upper ring 750 and the lower ring 755. In the illustrated embodiment, the sleeve 760 comprises an inner layer 762 and an outer layer 764 that define a pocket 766 there between. The pocket 766 is configured to receive gases from an interface tube 730. The lower ring 755 may be a hollow ring that is configured to receive gases from the pocket 766. In an embodiment, gases enter the pocket 766 from the interface tube 730, are communicated to the lower ring 755, and are released from the lower ring 755 via at least one gases outlet to the cavity. In an embodiment, at least one of the inner layer 762 and/or the outer layer 764 comprises a gases permeable material. This may allow gases to permeate out of the pocket and into the cavity and/or to the wound edge, respectively. In an embodiment, the lower ring 755 comprises a gases permeable material such that the gases diffuse through the lower ring 755 into the cavity. In an embodiment, the interface tube 730 is connected directly to the hollow lower ring 755. Thus, in an embodiment, the multi-layer sleeve 760 can be replaced with a single layer sleeve 760. In an embodiment, the sleeve 760 can be formed from a gases impermeable material.

In the illustrated embodiment, the upper ring 750 is configured to scavenge gases, such as smoke, or waste gases, from the cavity. The upper ring 750 may be configured to apply a suctioning force to the cavity to remove the gases. In an embodiment, the upper ring 750 comprises a vacuum source. In an embodiment, an external vacuum source is used to generate the suction, for example, a vacuum port within the operating theatre. In an embodiment, the upper ring 750 is a hollow ring that receives the scavenged gases from the cavity. The upper ring 750 is configured to be pneumatically coupled to a scavenging tube 770. The gases are removed from the cavity via the scavenging tube 770. The scavenging tube 770 removes the gases to a gases reservoir wherein the gases are filtered before exhausting to the atmosphere. In an embodiment, the gases are recirculated into the cavity. In some such embodiments, the gases are filtered to remove contaminants and/or entrained air before recirculation into the cavity.

In an embodiment, a valve 775 on the scavenging tube 770 controls the amount of gases removed from the cavity. This allows a minimum gases condition—such as gases concentration, temperature, and/or humidity—to be maintained within the cavity during the procedure. In an embodiment, multiple valves 775 are present in the system, for example, an inlet valve and an outlet valve. The inlet valve may be configured to control the flow rate of the gases entering the cavity via the interface tube 730. The outlet valve may be configured to control the flow rate of the gases leaving the cavity via the scavenging tube 770, with respect to the monitored pressure of the incoming gases. A higher flow rate of gases entering the cavity than leaving the cavity maintains a sufficient level of gases within the cavity.

Figure 8A:
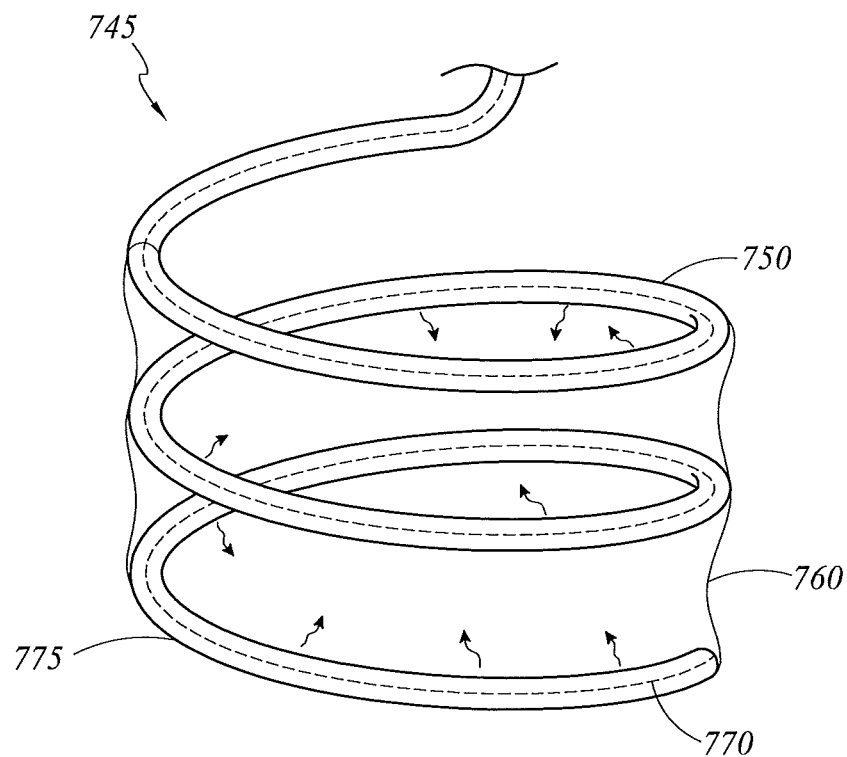
FIGS. 8A and 8B illustrate perspective views of a wound retractor including a spiral conduit according to embodiments of the present disclosure.
Figure 8B:
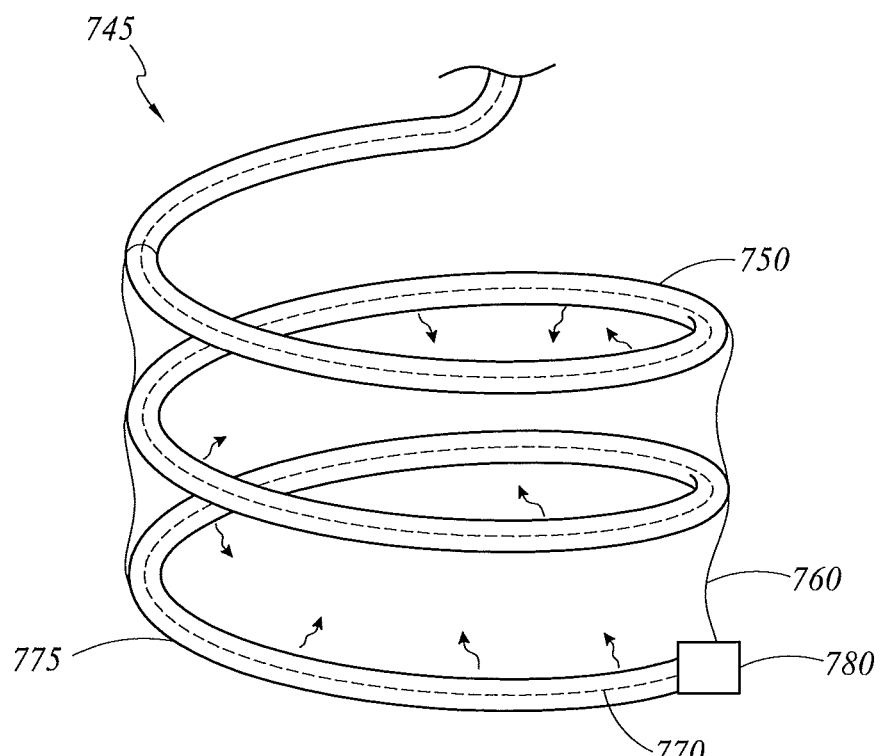

FIGS. 8A and 8B illustrate perspective views of a wound retractor 745 including a spiral conduit 750 according to embodiments of the present disclosure. The spiral conduit 750 is coiled around the wound retractor 745. The spiral conduit 750 is coated with the sleeve 760. In an embodiment, the spiral conduit 750 comprises a foamed material. In an embodiment, the spiral conduit 750 comprises a flexible spine 770. The flexible spine 770 can be adjusted or manipulated prior to insertion into the cavity. The adjustment can change the height, diameter or pitch of the spiral conduit 750. The flexible spine 770 can comprise, for example, metallic filaments, a spring, or a plastic bead. In an embodiment, use of a spring creates a tendency in the spiral conduit 750 to return to its relaxed state when compressed. Thus, the flexible spine 770 provides structure to the wound retractor 745, such that the sleeve 760 can hold the tissue in place within the cavity.

In an embodiment, the flexible spine 770 is enclosed within an outer sleeve 775. In an embodiment, the outer sleeve 775 can replace the flexible spine 770. The outer sleeve 775 can pneumatically connect with a gases source via an interface tube (not shown). In an embodiment, the outer sleeve 775 comprises a foamed material. In an embodiment, the spiral conduit 750 forms the interface. Gases can diffuse from the spiral conduit 750 or the outer sleeve 775 and into the cavity.

In an embodiment, the outer sleeve 775 is permeable to gases such that the gases can also diffuse into the wound edge. Thus, the wound edge also benefits from exposure to the gases.

In an embodiment, the gases can inflate the spiral conduit 750. Thus, the gases can provide additional structure to the spiral conduit 750 within the cavity. Inflation of the spiral conduit 750 causes additional tension to be applied to the sleeve 760. This enables further retraction of the tissue, thereby creating an enlarged workspace for the surgeon.

FIG. 8B illustrates an embodiment wherein the outer sleeve 775 is impermeable to gases and liquids. The outer sleeve 775 comprises a gases outlet 780 at the base that allows gases to enter the cavity. In an embodiment, the gases outlet 780 may comprise a valve. The valve may allow gases to enter the cavity once a predetermined pressure is exceeded in the outer sleeve 775. Gases entry at the base of the wound retractor 745 may fill the cavity with gases more effectively due to characteristics of the gases flow; for example, gases denser than air will expel air from the cavity as the cavity is filled from the bottom. As a result, this embodiment provides the advantage of better filling the cavity due to the location of the gases outlet 780.

Figure 9A:
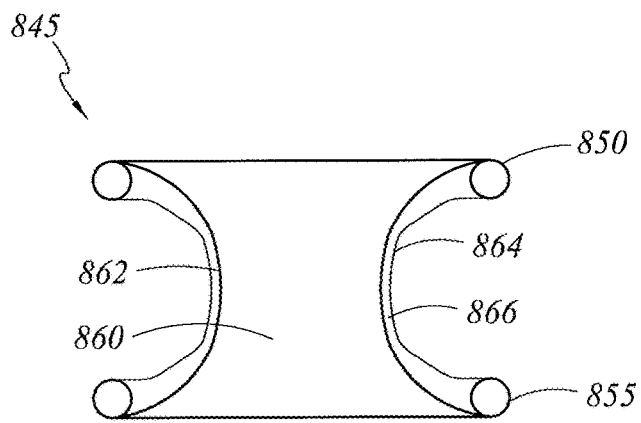
FIGS. 9A through 9D illustrate various views of a wound retractor including a sleeve defining a pocket with channels according to embodiments of the present disclosure.
Figure 9B:
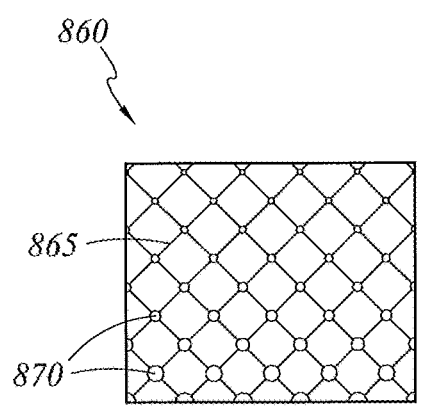
Figure 9C:
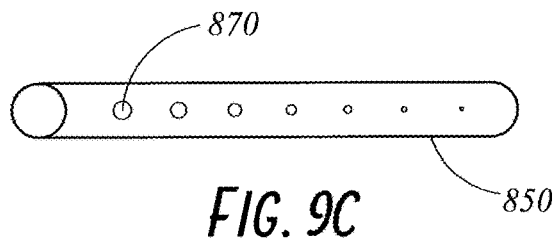
Figure 9D:
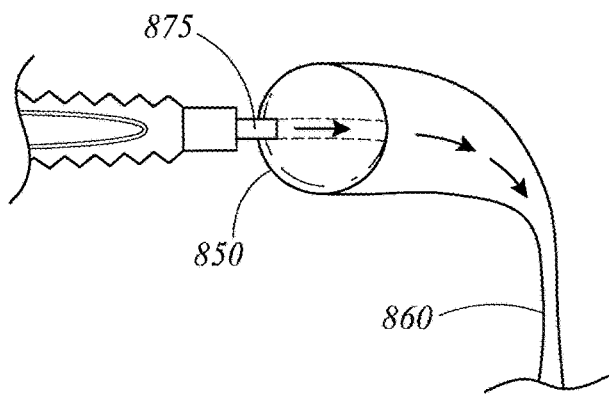

FIGS. 9A through 9D illustrate various views of a wound retractor 845 including a sleeve 860 defining a pocket 866, channels 865, and perforations 870 according to embodiments of the present disclosure. The wound retractor 845 also includes an upper ring 850 and a lower ring 855. FIG. 9A illustrates a cross-sectional view of the wound retractor 845. FIG. 9B illustrates a portion of the sleeve 860. FIG. 9C illustrates a detailed view of the upper ring 850. FIG. 9D illustrates a partial cross-sectional view of an embodiment where gases can be delivered into the sleeve 860 through the upper ring 850.

As best seen in FIG. 9A, the sleeve 860 comprises an inner layer 862 and an outer layer 864 with a pocket 866 defined in between. As illustrated in FIG. 9B, the sleeve 860 may include channels 865. The channels 865 may be located on the inner layer 862, the outer layer 864, or both layers. In an embodiment, the channels 865 are defined in the pocket 860 between the inner and the outer layers. The channels 865 define enclosed passageways through which gases may flow. The channels 865 may be arranged, as illustrated in FIG. 9B, in a grid-like pattern, although other arrangements, for example, channels extending in only a single direction, curved channels, spiral channels, etc., are possible.

In an embodiment, the sleeve 860 includes perforations 870 as illustrated in FIG. 9B. The perforations 870 may be located along the channels 865 and provide outlets for gases flowing within the channels. In an embodiment, the perforations 870 may alter in size depending on their location with regard to a gases inlet (for example, inlet 875 of FIG. 9D) to aid with distribution of the gases. For example, the perforations 870 distal to the gases inlet 875 may be larger than perforations 870 proximally located relative to the gases inlet 875.

FIG. 9D illustrates a gases inlet 875, through which the gases can enter the pocket 866 in the sleeve 860. In an embodiment, the channels 865 lead to perforations 870 in the sleeve 860, through which the gases diffuse. The channels 865 direct the gases flow along a desired path. In an embodiment, perforations in the inner layer 862 enable gases to be specifically delivered to the wound. In an embodiment, perforations in the outer layer 864 enable gases to be specifically delivered to the wound edge. In an embodiment, perforations in both the inner layer 862 and the outer layer 864 enable gases to be delivered to both the wound and the wound edge. FIG. 9C illustrates that, in an embodiment, the upper ring 850 (or the lower ring 855) may also include perforations 870 for delivering gases. The size of the perforations 870 on the ring may vary with distance from the inlet to control the distribution of gases. In an embodiment, at least one of the upper ring 850 and the lower ring 855 comprises directed openings to distribute the gases. In an embodiment, the sleeve 860, the upper ring 850, and the lower ring 855, each comprises perforations 870 to better distribute the gases. In an embodiment, the perforations 870 may be omitted, and the channels 865 and/or the sleeve 860 may comprise a gases permeable material.

The perforations 870 may be positioned on the inner layer 862 and/or the outer layer 864. When positioned on the inner layer 862, gases are distributed inside the cavity. When positioned on the outer layer 864, gases are distributed to the wound edge. In an embodiment, the perforations 870 may be evenly distributed on the wound retractor 845. In an embodiment, the perforations 870 may be distributed on only a portion of the wound retractor 845 (for example, a section of the sleeve 860).

As illustrated in FIG. 9D, in an embodiment, gases may enter the wound retractor 845 via an inlet in the upper ring 850 (or in the lower ring 855). In an embodiment, the sleeve 860 may include an inlet configured to receive gases into the pocket 860 and/or channels 865.

Embodiments of the wound retractor 845 replace traditional diffuser interface components by including a gases dispersal means within the wound retractor 845. This may reduce the number of items required during a procedure and, as such, reduce the complexity of setup and the number of steps required. This may also reduce the number of instruments that are positioned within the cavity, thereby improving the workspace of the surgeon. Features of the wound retractor 845 may be integrated into any other wound retractor described herein.

Figure 10:
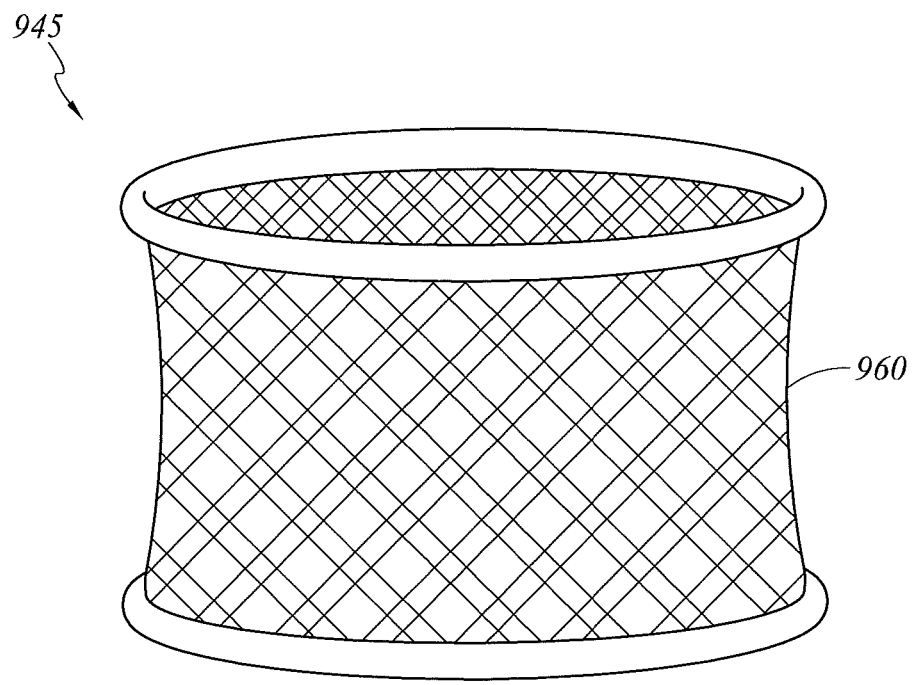
FIG. 10 illustrates a perspective view of a wound retractor configured to diffuse gases into a cavity and/or to a wound edge according to an embodiment of the present disclosure.

FIG. 10 illustrates a perspective view of a wound retractor 945 that is configured to diffuse gases into the cavity and/or to the wound edge. The wound retractor 945 includes an upper ring, a lower ring, and a sleeve 960 extending between and connecting the upper ring and the lower ring. The sleeve 960 may be formed from a gases permeable material such that gases can diffuse into the wound or the wound edge. In an embodiment, the sleeve 960 comprises an open cell foam. In an embodiment, the orientation of fibres in the material of the sleeve 960 can provide a tortuous path such that gases can diffuse through the sleeve 960 but contaminants are trapped and thus prevented from or substantially prevented from entering the wound edge area. In an embodiment, the sleeve 960 can be formed from gases permeable film, for example Tyvek or other spunbonded olefin fibers. The film can be chosen such that gases can pass through the film but contaminants that are larger than gases are occluded from passing through the film to the wound edge. Examples of such films include those commonly used in food packing, such as low-, linear low-, and high-density polyethylene (LDPE, LLDPE, and HDPE, respectively), polypropylene (PP), and biaxially oriented polypropylene (BOPP). The features of the sleeve 960 described in reference to FIG. 10 may be integrated into any of the other wound retractors described herein.

Figure 11:
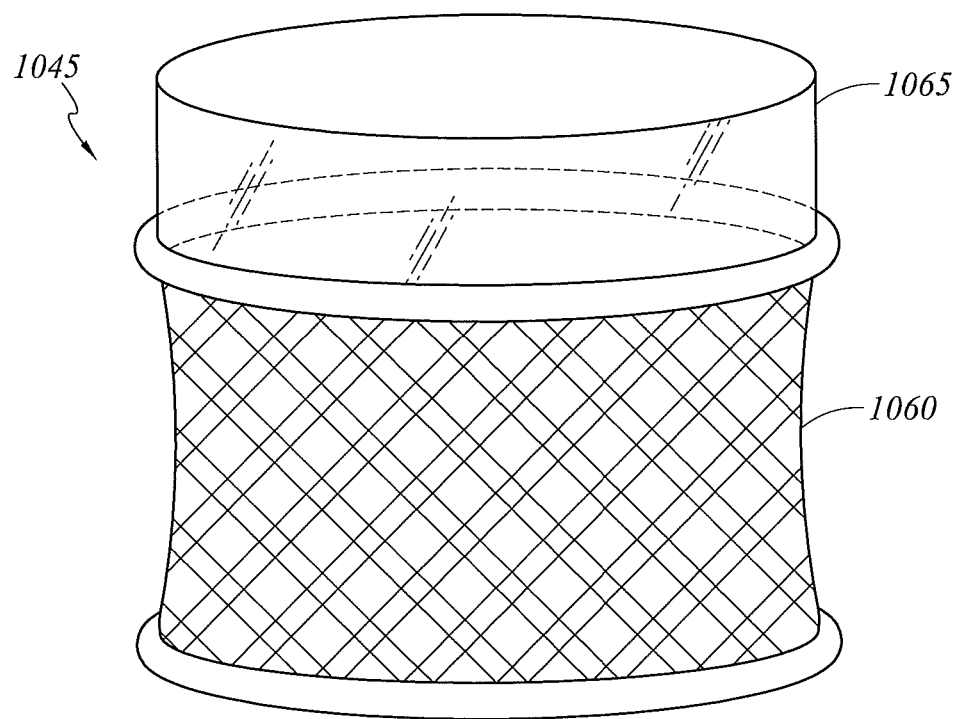
FIG. 11 illustrates a perspective view of a wound retractor including a sleeve extender according to an embodiment of the present disclosure.

FIG. 11 illustrates a wound retractor 1045 that includes an embodiment of a sleeve 1060 and a sleeve extension 1065. The sleeve extension 1065 can be used to increase the depth of the cavity. In an embodiment, the sleeve extension 1065 may be configured to increase the depth of the cavity by about 0.5 cm to about 10 cm, or to about 50 cm. This may be beneficial as it may increase the volume of gases that are contained within the cavity.

The sleeve extension 1065 can be formed from the same material as the sleeve 1060 (or any other sleeve described throughout this disclosure). In an embodiment, the sleeve extension 1065 may be made from a different material than that of the sleeve 1060. For example, the sleeve 1060 may comprise a gases permeable material while the sleeve extension 1065 may comprise a material that is impermeable to gases. The impermeability of the sleeve extension 1065 may reduce gases being lost to the atmosphere. This may be especially relevant in embodiments wherein the sleeve extension 1065 extends slightly above the wound. It is to be understood that the sleeve extension 1065 may be combined with other embodiments discussed herein.

In the illustrated embodiment of FIG. 11, the sleeve extension 1065 is formed integrally with the sleeve 1060. In other embodiments, however, the sleeve extension 1065 can be a separate piece. The sleeve extension 1065 can be coupled with the wound retractor 1045, for example, to an upper ring 1050 thereof, using, for example, adhesives, clipping, or hook and loop mechanisms.

In an embodiment, the sleeve extension 1065 is configured as a flexible, hollow sleeve. In this embodiment, the sleeve extension 1065 may be configured to inflate when supplied with gases from the gases source (in other words, when gases are pumped into the hollow space within the sleeve extension 1065). In an embodiment, the sleeve extension 1065 comprises a gases inlet to facilitate entry of gases into the sleeve extension 1065. In an embodiment, the gases inlet comprises a valve, for example, a one-way valve, to regulate the flow of gases into the sleeve extension 1065. Inflation of the sleeve extension 1065 causes the sleeve extension 1065 to be soft and pliable in use. This allows the surgeon to manipulate the sleeve extension 1065 during use. The sleeve extension 1065 is configured to couple with, for example, the wound retractor 1045 or any other wound retractor described herein or elsewhere via coupling mechanisms, such as those discussed above.

Figure 12:
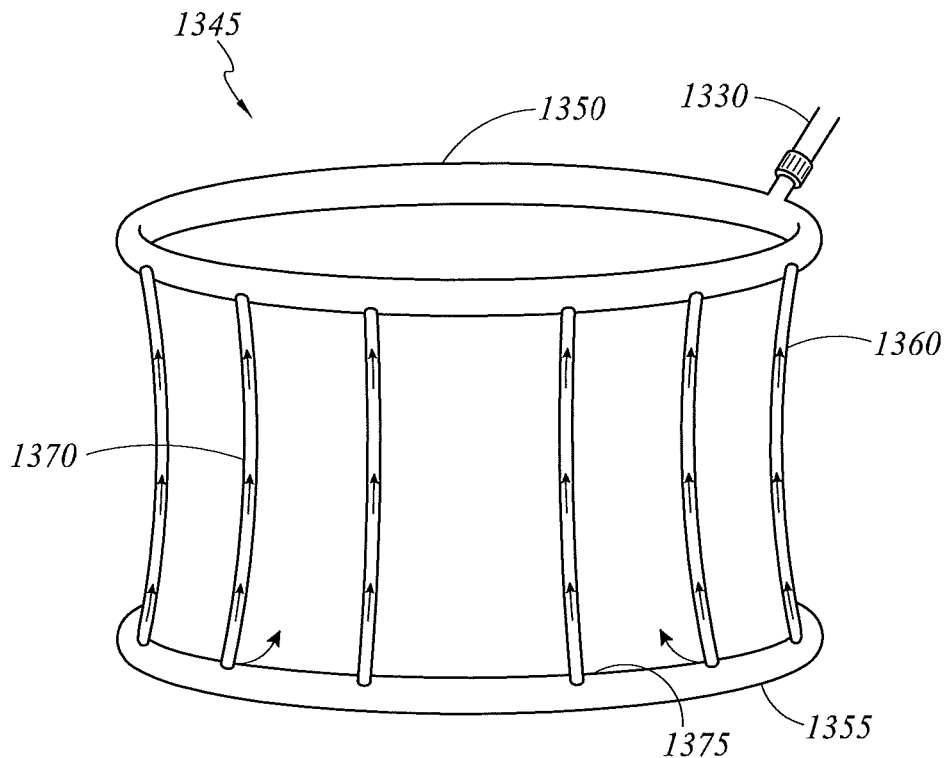
FIG. 12 illustrates a perspective view of a wound retractor including a plurality of channels pneumatically connecting an upper ring with a lower ring according to an embodiment of the present disclosure.

FIG. 12 illustrates a perspective view of a wound retractor 1345 including channels 1370 that pneumatically connect an upper ring 1350 with a lower ring 1355 according to an embodiment of the present disclosure. In an embodiment, the channels may extend along a sleeve 1360 extending between and connecting the upper ring 1350 and the lower ring 1355. In the illustrated embodiment, the upper ring 1350 couples with an interface tube 1330 via a gases inlet. In the illustrated embodiment, the upper ring 1350 is hollow, providing a pathway through which gases from the interface tube 1330 pass. The sleeve 1360 includes vertically extending channels 1370. In an embodiment, the vertically extending channels 1370 extend from the upper ring 1350 to the lower ring 1355. That is, the channels 1370 extend between the upper ring 1350 and the lower ring 1355 in a direction that is perpendicular to that of either ring. The channels 1370 pneumatically connect the upper ring 1350 with the lower ring 1355. Gases move from the upper ring 1350, through the channels 1370, to the lower ring 1355. In an embodiment, the channels 1370 comprise hollow spines that transfer gases from the upper ring 1350. In an embodiment, the lower ring 1355 may include an inlet for connecting the interface tube 1330 and the channels 1370 may allow gases to flow from the lower tube 1350 to the upper tube 1370. In an embodiment, the channels 1370 need not be vertical. For example, the channels may extend at an angle with respect to vertical, may include curved sections, etc. In an embodiment, the wound retractor 1345 may include only a single channel 1370, while in other embodiments, the wound retractor 1345 may include a plurality of channels 1370.

In an embodiment, the channels 1370 are permeable to gases, such that the gases can diffuse to the space between the channels 1370 and to the wound edge. In an embodiment, the channels 1370 comprise directed openings or perforations to move gases to the space between the channels 1370 and to the wound edge. In an embodiment, the lower ring 1355 comprises a foam material, or directed openings, such that the gases can diffuse through the lower ring 1355. In an embodiment, the lower ring 1355 comprises at least one outlet 1375 through which the gases can move into the cavity. In an embodiment, at least one of the outlets 1375 allows gases to also move into the wound edge area. In an embodiment, the outlets 1375 may be shaped to encourage the gases to exit the lower ring 1355 in a direction that encourages filling of the cavity.

In an alternative embodiment, the channels 1370 take the form of a spine that extends vertically between the upper ring 1350 and the lower ring 1355. The upper ring 1350 comprises a gases permeable structure while still providing rigidity to the wound retractor 1345. Thus, gases are configured to diffuse from the upper ring 1350 into the space created between the spines. As a result, gases are exposed to the wound edge. The lower ring 1355, as described above, enables movement of gases between the wound edge and the cavity, either via a gases permeable foam material or by outlets 1375 in the lower ring 1355. In an embodiment, the sleeve 1360 comprises a gases permeable material to diffuse gases between the wound edge and the cavity. The features described in reference to FIG. 12 may be incorporated into any of the wound retractors described throughout this disclosure.

Figure 13:
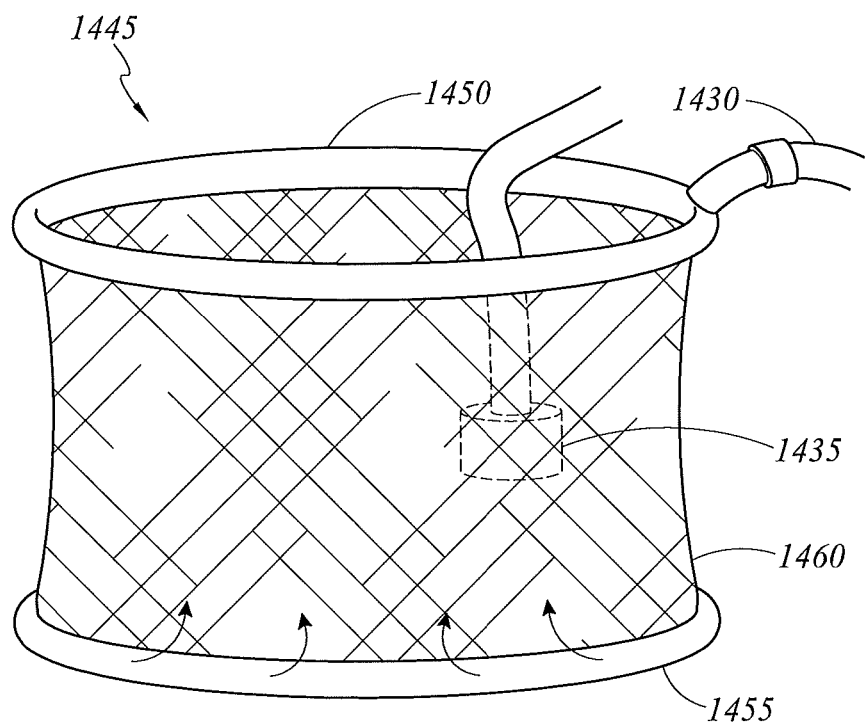
FIG. 13 illustrates a perspective view of a wound retractor including an absorbent sleeve according to an embodiment of the present disclosure.

FIG. 13 illustrates a perspective view of a wound retractor 1445 including an absorbent sleeve 1460 according to an embodiment of the present disclosure. In the illustrated embodiment, the wound retractor 1445 includes an upper ring 1450, a lower ring 1455, and the sleeve 1460 extending between and connecting the upper ring 1450 and the lower ring 1455. The sleeve 1460 is made from an absorbent material, for example a foamed plastic polymer. In use, the absorbent sleeve 1460 can be soaked in a solution prior to insertion of the wound retractor 1445. The sleeve 1460 absorbs the solution and, when in place in the wound, delivers the solution to the wound edge. The solution may be, for example, an alcohol, a therapeutic, or an acidic solution. In an embodiment, the sleeve 1460 may further include an outer layer or coating comprising the solution, such that the wound retractor 1445 is pre-packaged with the solution.

In an embodiment, alcohol solutions can be used for wound preparation prior to the procedure, which may reduce the steps required to prepare the wound for surgery. In an embodiment, the sleeve 1460 can be soaked in a therapeutic solution that is applied indirectly to the wound by the wound retractor 1445. For example, the wound retractor 1445 could be soaked in any one of an anaesthetic substance, an anti-inflammatory substance or an antibacterial substance. In an embodiment, soaking the sleeve 1460 in an acidic solution encourages oxygen release into the tissue via the Bohr Effect, as discussed elsewhere herein. This may lead to reduced risk of surgical site infection and improve the recovery of the patient 140. In an embodiment, the sleeve 1460 is soaked in an anti-adhesive substance. It is to be understood that the sleeve 1460 can be soaked in any combination of the substances described above or other suitable solutions. The features of the absorbent sleeve 1460 described in reference to FIG. 13 may be incorporated into any of the other wound retractors described herein.

In an embodiment, the wound retractor 1445 receives a diffuser interface 1435 that connects with a gases source and provides gases to the cavity. In an embodiment, the upper ring 1450 takes the place of the diffuser interface 1435 by connecting to an interface tube 1430 provides gases to the upper ring 1450. The upper ring 1450, thus, may diffuse gases into the cavity. The upper ring 1450 may be made from, for example, a gases permeable material, as discussed in the embodiments above.

Figure 14A:
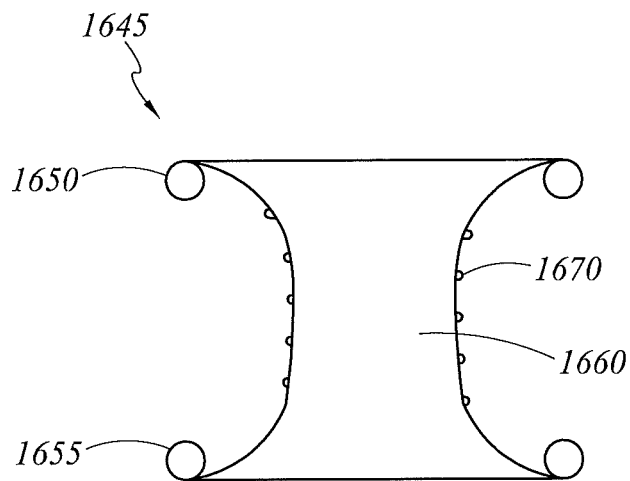
FIGS. 14A through 14C illustrate cross-sectional views of a wound retractor including a rib on a sleeve according to embodiments of the present disclosure.
Figure 14B:
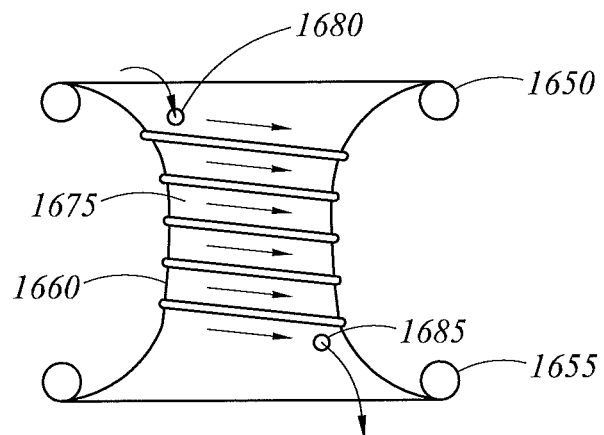
Figure 14C:
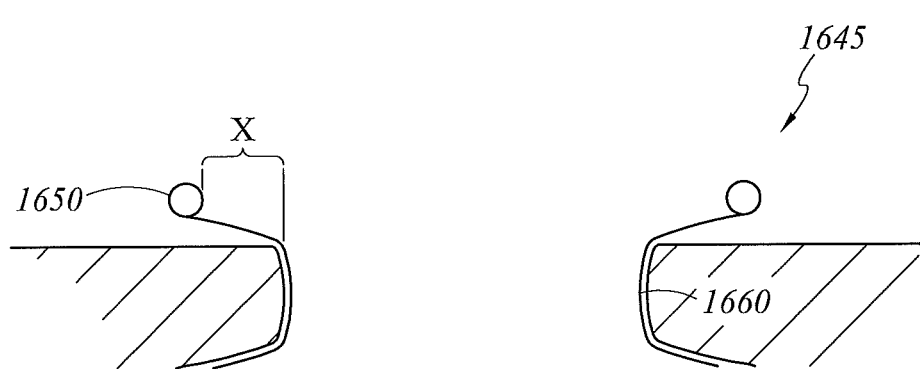

FIGS. 14A through 14C illustrate cross-sectional views of a wound retractor 1645 including a rib 1670 on a sleeve according to embodiments of the present disclosure. The wound retractor 1645 includes an upper ring 1650, a lower ring 1655, and a sleeve 1660 extending between and connecting the upper ring 1650 and the lower ring 1655. In the illustrated embodiment, the sleeve 1660 includes a rib 1670 which is continuously wrapped around the outside of the sleeve 1660. The rib 1670 may be formed from a plastics material. The rib 1670 may be semi-rigid, such that it can hold the sleeve 1660 out from the wall of the wound edge. That is, the rib 1670 is configured to contact the wound edge and separate the sleeve 1660 therefrom. Thus, spaces between the rib 1670 provide a pathway 1675 (as illustrated with arrows in FIG. 14B) through which gases can flow between the sleeve 1660 and the wound edge. The pathway 1675 may cause gases to flow spirally around the sleeve 1660 as shown by the arrows in FIG. 14B. The depth of the pathway 1675 is chosen such that it does not negatively impact the workspace of the surgeon. In an embodiment, the gases are exposed to the wound edge as they move along the pathway 1675. The rib 1675 may be configured in a number of ways. For example, it may be configured as a single spiral-wrapped rib as illustrated, for example, in FIG. 14B. In other embodiments, the wound retractor 1645 may comprise a plurality of ribs.

The gases may enter the pathway 1675 through a gases inlet 1680 located in the sleeve 1660. The gases may travel through the pathway 1675 and leave via a gases outlet 1685. In an embodiment, gases exiting the outlet 1685 are deposited into the cavity. Each of the gases inlet 1680 and the gases outlet 1685 may comprise a hole through the sleeve 1660. In an embodiment, one or both of the gases inlet 1680 and the gases outlet 1685 may comprise a valve. In an embodiment, one of the gases inlet 1680 and the gases outlet 1685 may comprise a hole and the other a valve. The gases inlet 1680 connects the gases flow with the pathway 1675. The gases outlet 1685 connects the gases flow with the cavity. In an embodiment, the gases inlet 1680 may receive gases from the upper ring 1650. In an embodiment, the gases outlet 1685 may deposit gases into or near the lower ring 1655.

In the illustrated embodiment, the gases inlet 1680 is located near the top of the sleeve 1660 and the gases outlet 1685 is located near the bottom of the sleeve 1660. In an embodiment, the gases may flow in the reverse direction. Thus, the gases inlet 1680 may be located near the bottom of the sleeve 1660 and the gases outlet 1685 may be located near the top of the sleeve 1660. The gases are supplied to the wound retractor 1645 from a gases source, such as, for example, the gases source 105.

In an embodiment, the gases inlet 1680 and the gases outlet 1685 are both positioned at or near the same height on the sleeve 1660. For example, both the gases inlet 1680 and the gases outlet 1685 are located at or near the bottom of the sleeve 1660 or at or near the top of the sleeve 1660. Thus, the pathway 1675 comprises a loop, dual pathway, or return pathway, such as, for example, a double helix. In an embodiment, the pathway 1675 exposes the gases to the wound edge before supplying the gases to the cavity.

Once the gases leave the pathway 1675, they are supplied to the cavity. In an embodiment, perforations in the sleeve 1660 pneumatically connect the pathway 1675 with the cavity. The perforations may alter in size along the sleeve

1660. For example, the perforations proximal the gases inlet 1680 may be smaller than perforations distal to the gases inlet. The size of the perforations may incrementally change with increasing distance from the gases inlet. As a result, the gases may leak out of the perforations, while maintaining the backpressure within the pathway 1675. In an embodiment, the sleeve 1660 comprises a gases permeable material. In an embodiment, the sleeve 1660 comprises a gases impermeable material.

In an embodiment, the rib 1670 comprises a gases permeable material. In an embodiment, the rib 1670 comprises directed openings. Thus, gases from within the pathway 1675 diffuse via the rib 1670 into the cavity. In an embodiment, the rib 1670 forms the pathway 1675. Thus, the gases travel via the rib 1670 to the gases outlet 1685, where the gases are distributed to the cavity. In an embodiment, the rib 1670 is permeable to gases such that the gases diffuse into the wound edge as they travel along the rib 1670. In an embodiment, the rib 1670 comprises perforations to encourage the gases to leak into the wound edge.

FIG. 14C illustrates an example embodiment of the wound retractor 1645 wherein the upper ring 1650 is displaced from the sleeve 1660 by a distance x due to the tension in the upper ring 1650.

Figure 15A:
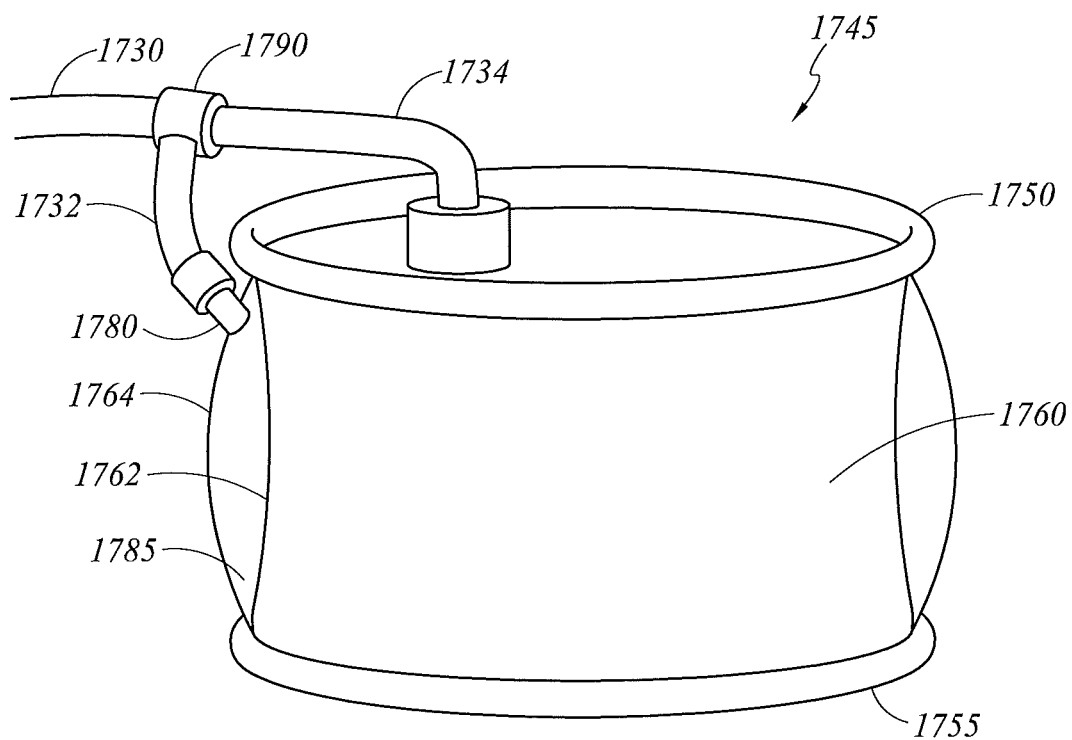
FIGS. 15A through 15C illustrate perspective views of a wound retractor including bifurcated interface tubes according to embodiments of the present disclosure.
Figure 15B:
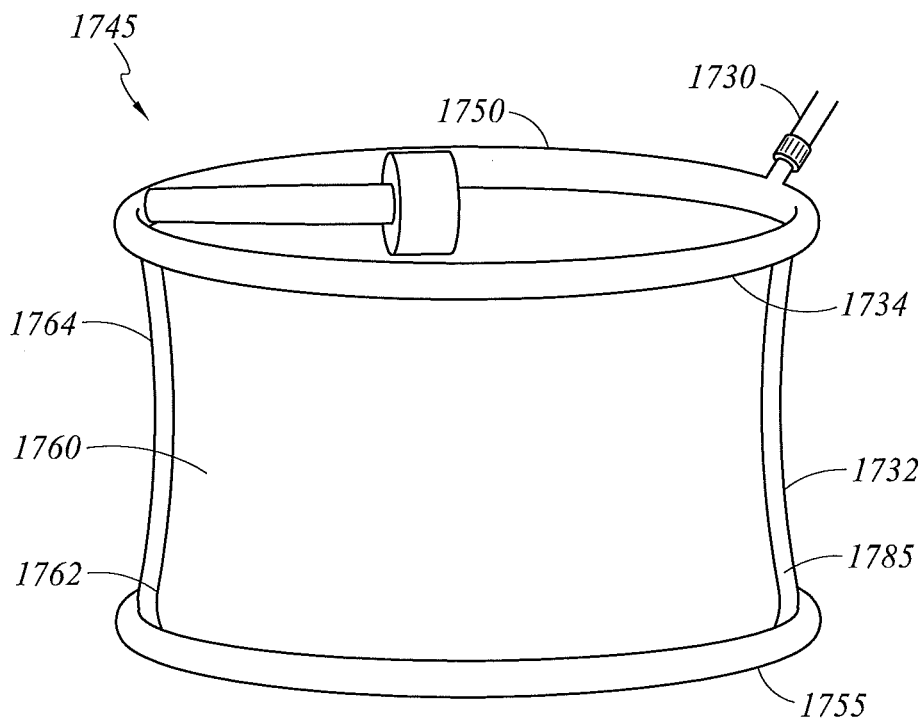
Figure 15C:
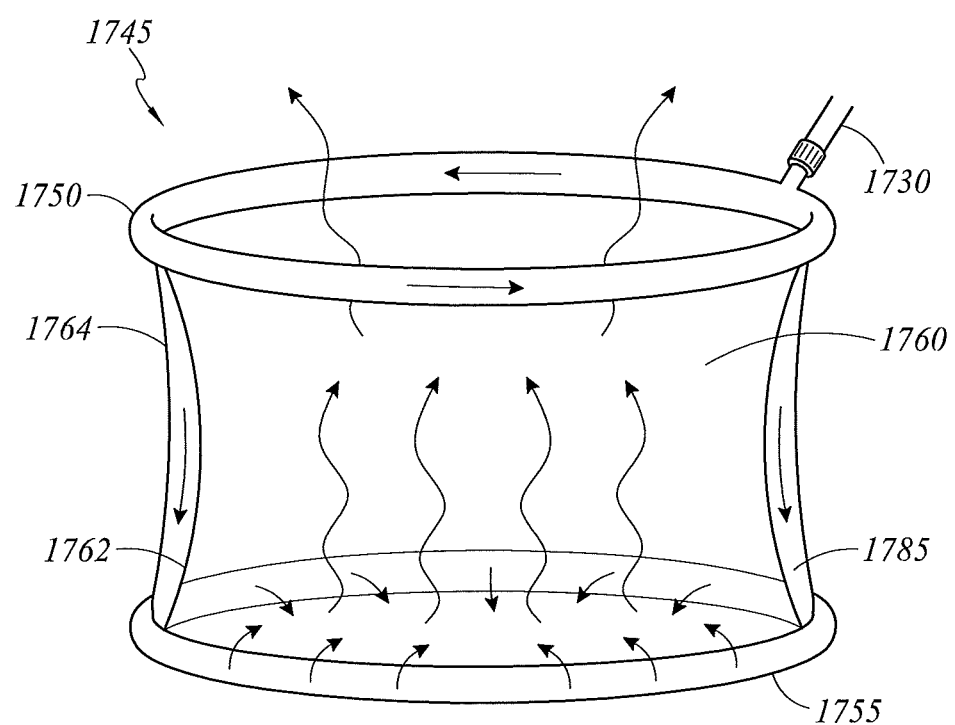

FIGS. 15A through 15C illustrate perspective views of a wound retractor 1745 including bifurcating interface tubes according to embodiments of the present disclosure. The wound retractor 1745 includes an upper ring 1750, a lower ring 1755, and a sleeve 1760 extending between and connecting the upper ring 1750 and the lower ring 1755. The sleeve 1760 may comprise a material that is impermeable to gases.

As illustrated in FIG. 15A, the sleeve 1760 may comprise an inner layer 1762 and an outer layer 1764. The inner layer 1762 and the outer layer 1764 may define a pocket 1785 there between. The wound retractor 1745 further comprises an interface tube 1730. As illustrated in FIG. 15A, the interface tube 1730 is a bifurcating tube. The interface tube 1730 comprises a first leg 1732 and a second leg 1734. The first leg 1732 of the interface tube 1730 is configured to pneumatically connect with a gases inlet 1780 near the upper ring 1750. The gases inlet 1780 may be pneumatically connected with the pocket 1785. The gases are thus provided to the pocket 1785 from the interface tube 1730. The second leg 1734 of the interface tube 1730 is configured to connect with a conventional diffuser or a diffuser interface comprising directed openings. The second leg 1734 may be configured to provide gases to the cavity. In an embodiment, the diffuser can be, for example, flat, or shaped as a paddle, which enables it to be tucked into the wound retractor 1745 and out of the way of the surgeon during the procedure. In an embodiment, the diffuser comprises directed openings, and thus the shape can be optimised to fit unobtrusively within the wound retractor 1745. It is to be understood that different diffuser shapes or configurations, or combinations of shapes can also be used.

In an embodiment, the outer layer 1764 of the sleeve 1760 is gases permeable such that gases are provided from the pocket 785 to the wound edge. In an embodiment, the inner layer 1762 of the sleeve 1760 can be made from a gases permeable material. Thus, gases can be provided to the pocket 1785 and can diffuse into the cavity via the inner layer 1762 of the sleeve 1760. Alternatively, gases can be provided to the cavity, and can diffuse through the inner layer 1762 and the outer layer 1764 of the sleeve 1760 to the wound edge. In an embodiment, the pocket 1785 is formed between the inner layer 1762 and the wound edge. Thus, gases diffuse directly to the wound edge. As discussed, in an embodiment, the inner layer 1762 may comprise a gases permeable material to allow gases to diffuse into the cavity. In an embodiment, the inner layer 1762 and/or the outer layer 1764 of the sleeve 1760 are gases impermeable. In an embodiment, the inner layer 1762 and/or the outer layer 1764 of the sleeve 1760 may include perforations or directed openings that allow gases to flow there through.

FIG. 15A also illustrates a control mechanism that can be used to control the distribution of the gases between the first leg 1732 and the second leg 1734. The control mechanism can take the form of, for example, a pressure valve 1790. The control mechanism acts to control the proportion of the gases flow that enters the cavity compared with the pocket 1785. In an embodiment, the control mechanism may be located at the junction of the first leg 1732 and the second leg 1734. In an embodiment, each of the first leg 1732 and the second leg 1734 include valves to control the flow therethrough.

FIG. 15B illustrates an example embodiment in which the interface tube 1730 is configured to pneumatically connect with the upper ring 1750. In this embodiment, gases move from the interface tube 1730 to the hollow upper ring 1750 and into the pocket 1785 within the sleeve 1760. For example, the hollow upper ring 1750 may include directed openings, perforations, or a gases permeable material that allows gases to flow from the upper ring 1750 into the pocket 1785.

FIG. 15C illustrates an example embodiment of the wound retractor 1745 wherein the interface tube 1730 delivers gases to the lower ring 1755. In an embodiment, the interface tube 1730 couples with the upper ring 1750. The upper ring 1750 is hollow such that the gases can be delivered to the upper ring 1750, into the pocket 1785, and into the lower ring 1755. In an embodiment, the interface tube 1730 couples with the sleeve 1760 such that gases are delivered directly into the pocket 1785. The gases may be transferred to the lower ring 1755 from the pocket 1785, from where they are diffused. In an embodiment, a pneumatic connection exists between the upper ring 1750 and the pocket 1785. As a result, gases delivered to the upper ring 1750 move to the lower ring 1755 via the pocket 1785.

In an embodiment, the lower ring 1755 pneumatically couples with the pocket 1785. In an embodiment, the upper ring 1750 acts as a reservoir for the gases. An additional tube or tube extension can transport the gases from the upper ring 1750 to the lower ring 1755. The lower ring 1755 is at least partially hollow. Gases diffuse from the lower ring 1755 into the cavity. At least a part of the lower ring 1755 comprises a gases permeable material, such as, for example, directed openings, foam or open cell foam. Diffusing from the lower ring 1755 enables manipulation of the upper ring 1750 without impacting gases delivery. In an embodiment, the features described in reference to FIGS. 15A-15C may be incorporated into any of the other embodiments of wound retractors described herein.

Figure 16:
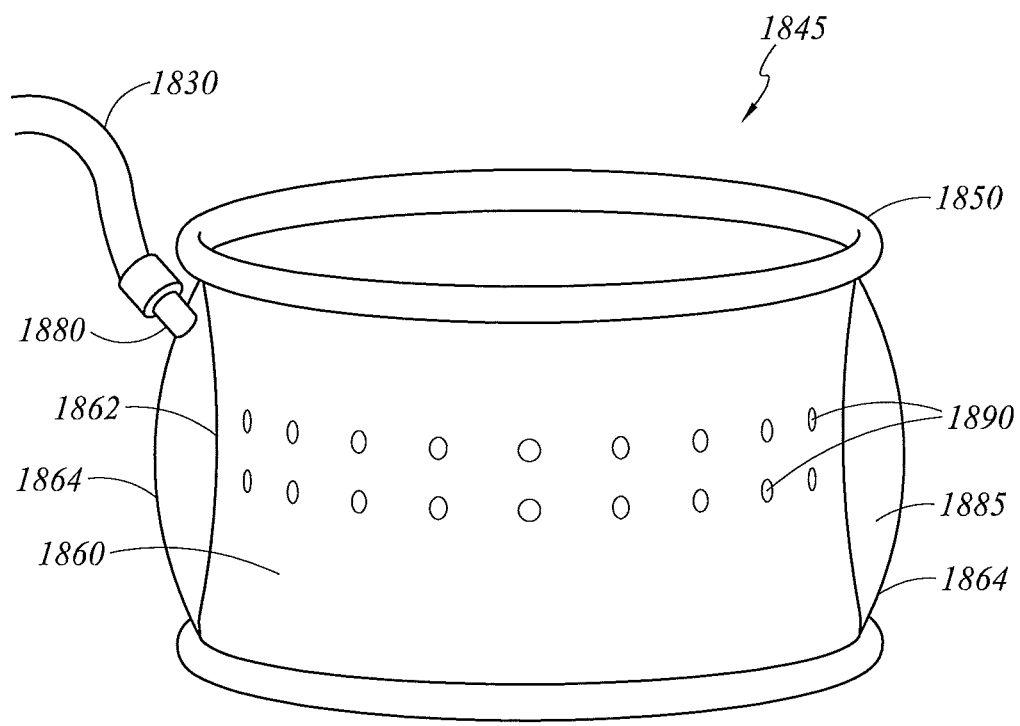
FIG. 16 illustrates a perspective view of a wound retractor configured to deliver gases through a pocket in a sleeve according to an embodiment of the present disclosure.

FIG. 16 illustrates a perspective view of a wound retractor 1845 configured to deliver gases through a pocket in a sleeve 1860 according to an embodiment of the present disclosure. The wound retractor 1845 includes an upper ring 1850, a lower ring 1855, and the sleeve 1860 extending between and connecting the upper ring 1850 and the lower ring 1855. The sleeve 1860 comprises an inner layer 1862 and an outer layer 1864, which define a pocket 1885. The pocket 1885 is configured to receive gases from a gases inlet 1880. The gases inlet 1880 is configured to pneumatically couple with an interface tube 1830. In an embodiment, the pocket 1885 is defined as the space between the inner layer 1862 and the wound edge. Thus, gases supplied to the pocket 1885 diffuse directly to the wound edge. In an embodiment, the inner layer 1862 is permeable to gases. Thus, gases supplied to the cavity diffuse through the inner layer 1862 to the wound edge.

In the illustrated embodiment, the inner layer 1862 of the sleeve 1860 comprises perforations 1890 that pneumatically couple the pocket 1885 with the cavity. As a result, gases that enter the pocket 1885 via the gases inlet 1880 move from the pocket 1885 to the cavity via the perforations 1890. This may reduce the risk of external contamination within the wound or wound edge. The number and/or distribution of perforations 1890 can be varied. In an embodiment, the perforations 1890 can be of varying sizes and shapes. For example, the perforations 1890 can be between 0.001 mm and 1.0 mm in diameter. In an embodiment, the perforations 1890 are between 0.001 mm and 0.01 mm. In an embodiment, the perforations 1890 are between 0.01 mm and 1.0 mm. In an additional example, the perforations 1890 are substantially circular in shape. The perforations 1890 may be configured to cause a backpressure to exist as gases move into the cavity from the pocket 1885. As pressurisation of the gases occurs via the easiest path, the gases flow may change over the course of the procedure.

A diffuser may be configured to deliver gases to the pocket 1885. Thus, the diffuser may be positioned within the pocket 1885 in an embodiment. This may be advantageous because when the diffuser is not positioned within the cavity this may reduce inconvenience to the surgeon because the diffuser is not within the workspace area. Thus, the wound retractor 1845 may be used to reduce the total number of instruments within the cavity.

In an embodiment, the outer layer 1864 is permeable to gases. This allows the gases within the pocket 1885 to diffuse through the outer layer 1864 to the wound edge. As a result, the wound edge is exposed to heated and humidified gases. The features of the wound retractor 1845 may be integrated into any other wound retractor described herein.

Figure 17:
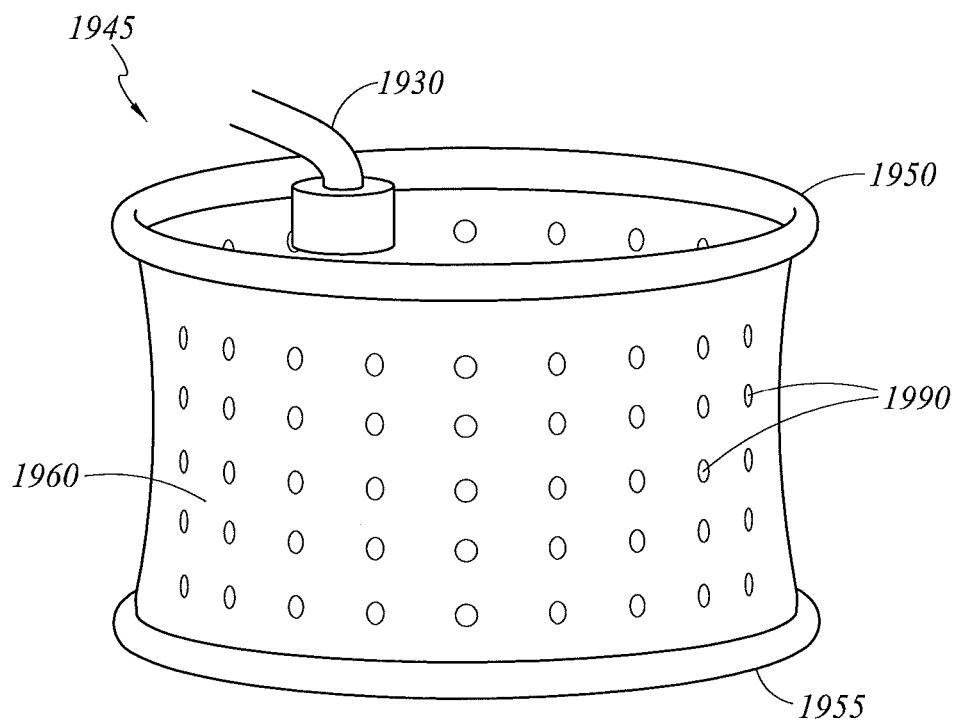
FIG. 17 illustrate a perspective view of a wound retractor including a perforated sleeve according to an embodiment of the present disclosure.

FIG. 17 illustrates a perspective view of a wound retractor 1945 including a perforated sleeve according to an embodiment of the present disclosure. The wound retractor 1945 comprises an upper ring 1950, a lower ring 1955, and a sleeve 1960 extending between and connecting the upper ring 1950 and the lower ring 1955. The sleeve 1960 includes perforations 1990, such as those described in reference to FIG. 16. The perforations 1990 are configured to pneumatically couple the cavity with the area of the wound edge. That is, gases in the cavity can flow through the perforations 1990 and contact the wound edge. In the illustrated embodiment, gases enter the cavity from a diffuser positioned at the end of an interface tube 1930 within the cavity. The gases move through the perforations 1990 into the area of the wound edge. Thus, with the wound retractor 1945 both the tissues within the cavity and at the wound edge may be exposed to heated and humidified gases. The features of the wound retractor 1945 may be integrated into any other wound retractor described herein.

Figure 18A:
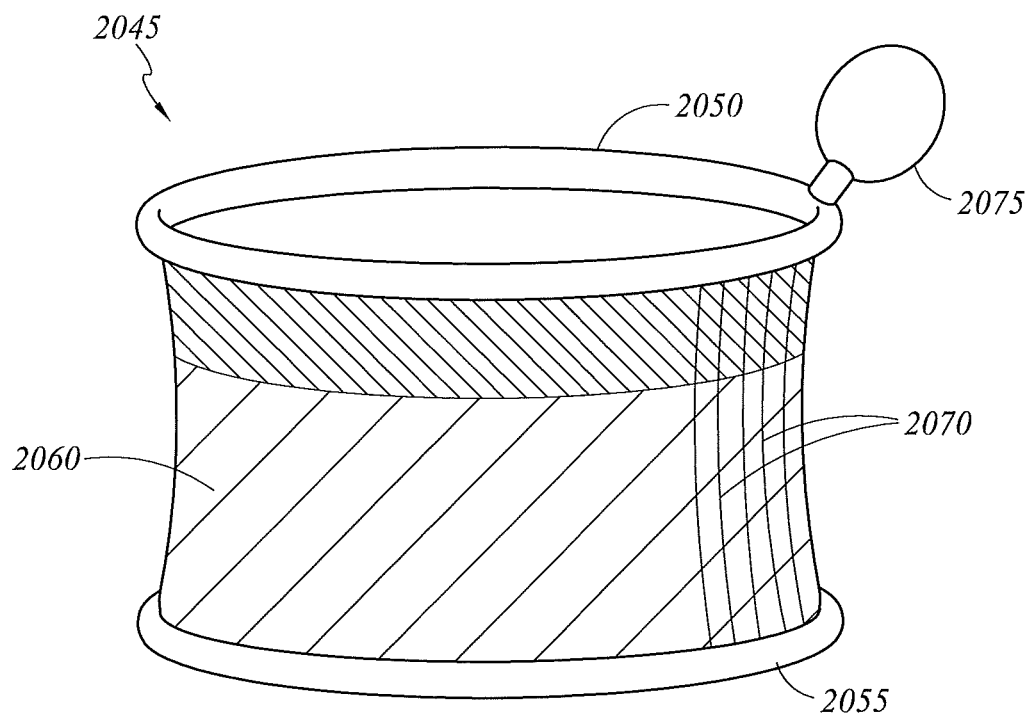
FIGS. 18A and 18B illustrate perspective views of a wound retractor configured to wick and/or heat liquid according to embodiments of the present disclosure.

FIG. 18A illustrates a perspective view of a wound retractor 2045 configured to wick and/or liquid according to an embodiment of the present disclosure. The wound retractor 2045 includes an upper ring 2050, a lower ring 2055, and a sleeve 2060 extending between and connecting the upper ring 2050 and the lower ring 2055. The sleeve 2060 may include channels 2070 formed therein. In an embodiment, the channels 2070 are positioned on the outside of the sleeve 2060. In an embodiment, the channels 2070 are positioned on the inside of the sleeve 2060. In an embodiment, the channels 2070 are formed by small tubes welded to a surface of the sleeve 2060. In an embodiment, the channels 2070 are formed by bonding multiple concentric sleeves 2060 together from top to bottom at intervals around the circumference to create vertical channels between the sleeves 2060. The channels 2070 are configured to wick liquid such as liquid source 2075. In an embodiment, the channels 2070 are further configured to store the water or other liquid. A reservoir or feed set may act as the water source 2075.

In an embodiment, the wound retractor 2045 includes a heating mechanism that heats the water within the channels 2070. In an embodiment, the wound retractor 2045 includes a heating mechanism but does not include the channels 2070. In an embodiment, the heating mechanism comprises a heater wire. The heater wire can be connected to an external power source. A connector at or near the lower ring 2055 can connect the heater wire with the external power source. In an embodiment, the connector can be positioned at or near the upper ring 2050. The heater wire can be substantially wrapped around the sleeve 2060. In an embodiment, the heater wire can be configured to heat at least a portion of the sleeve 2060. In an embodiment, a plurality of heater wires can extend from the lower ring 2055. In an embodiment, the plurality of heater wires can be at least partially associated with the channels 2070. The heater mechanism may facilitate evaporation of the water within the channels 2070.

In an embodiment, the sleeve 2060 can be heated passively, such as, for example, using body heat. For example, the sleeve 2060 can comprise a thermally conductive material. Because the sleeve 2060 is in close proximity to body tissue, heat from the body can warm the sleeve 2060. This may facilitate evaporation of the water within the channels 2070.

In an embodiment, the sleeve 2060 can be coated in a chemical layer. Once activated, the chemical layer causes an exothermic reaction. The reaction causes heat to be applied to the water within the channels 2070. Thus, the water within the channels 2070 is heated and humidified. Example chemicals and activations methods are described in greater detail below.

Figure 18B:
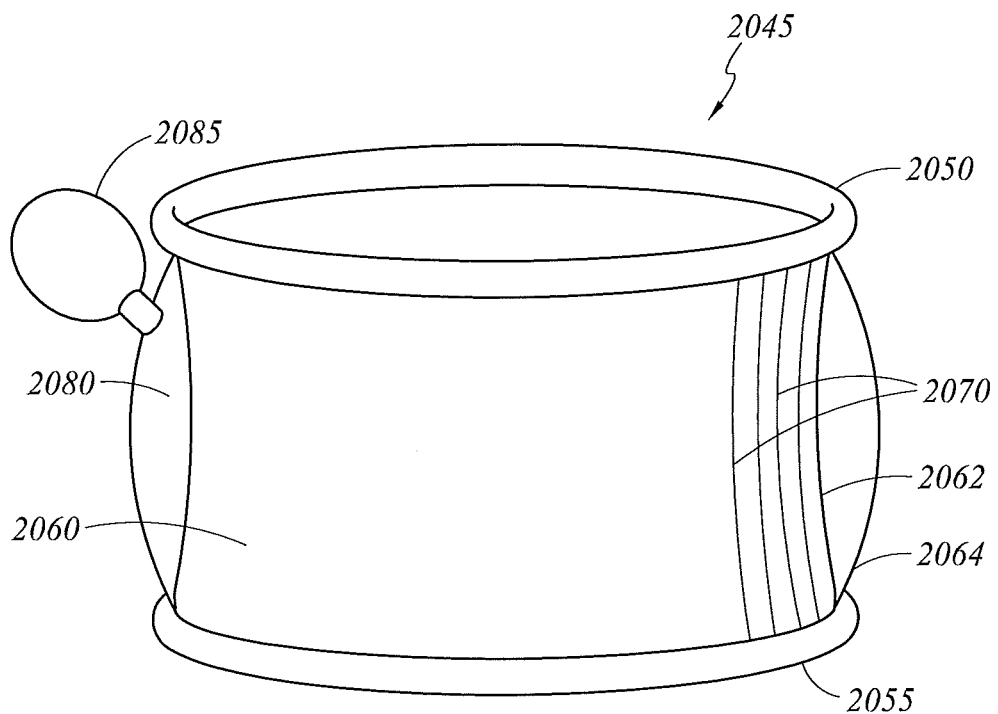

FIG. 18B illustrates an embodiment wherein the sleeve 2060 includes an inner layer 2062 and an outer layer 2064 with a pocket 2080 being defined therein. Chemicals can be integrated into the pocket 2080. As above, activation of the chemicals may cause an exothermic reaction, causing the water within the channels 2080 to vaporise. The channels 2080 can be located on the inner layer 2062, the outer layer 2064, or both the inner layer 2062 and the outer layer 2064. Thus, the exothermic reaction may indirectly heat the channels 2070.

Activation mechanisms comprise, for example, an ampule 2085 comprising a second chemical (for example, as illustrated in FIG. 18B). The ampule 2085 may be located externally from the wound retractor 2045. In an embodiment, the ampule 2085 may be integrated within the sleeve 2060 or the pocket 2080. The second chemical, when combined with the chemicals of the sleeve 2060, may cause an exothermic reaction. To combine the chemicals, the ampule 2085 may be compromised or broken. In an example, a flexible ampule 2085 may comprise a valve or narrowing such that the second chemical is unable to combine with the first. A force can be applied to the ampule 2085. For example, the ampule 2085 may be squeezed to urge the second chemical to interact with the first. In a further example, an external power source can apply heat to the chemicals to activate the exothermic reaction. In yet a further example, body heat from the patient 140 may activate the exothermic reaction of the chemicals.

In an embodiment, positioning the heating mechanism at or near the lower ring 2055 may be beneficial because force is often applied to the upper ring 2050 to tension the sleeve 2060, such as, for example, rolling the upper ring 2050. Thus, positioning components at or near the lower ring 2055 may provide a more consistent position, thus improving the usability of the wound retractor 2045. This position is less susceptible to change upon installation or during manipulation of the wound retractor 2045 within the cavity.

Figure 19:
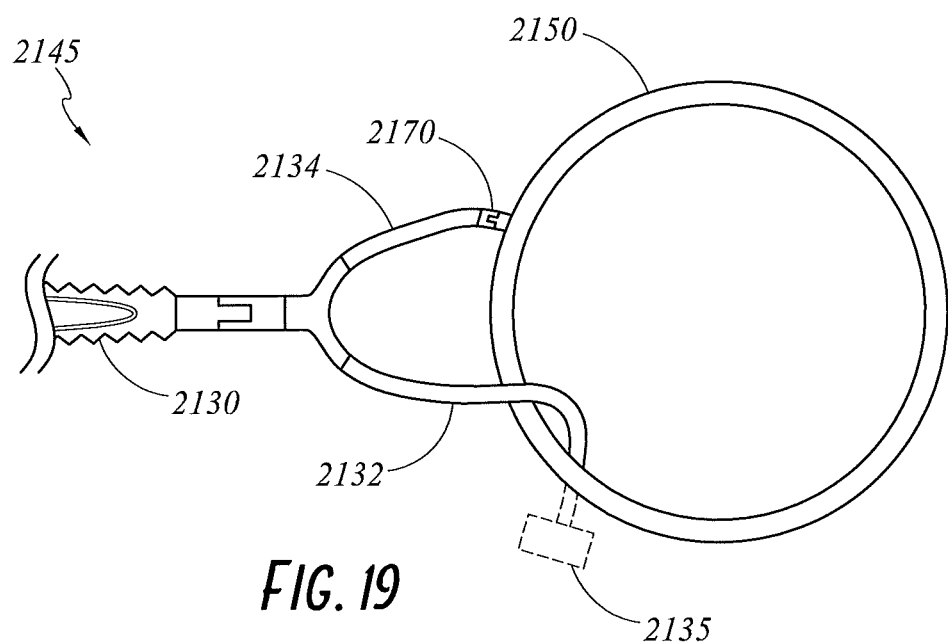
FIG. 19 illustrates a top view of a wound retractor including a bifurcating interface tube according to an embodiment of the present disclosure.

FIG. 19 illustrates a top view of a wound retractor 2145 including a bifurcating interface tube according to an embodiment of the present disclosure. The wound retractor 2145 includes an upper ring 2150 and an interface tube 2130. The interface tube 2130 comprises a bifurcating tube. Thus, the interface tube 2130 comprises a first leg 2132 and a second leg 2134. The first leg 2132 comprises a diffuser interface 2135. In an embodiment, the diffuser interface 2135 may be a conventional diffuser. In an embodiment, the diffuser interface 2135 comprises directed openings to distribute the gases. The diffuser interface 2135 may be positioned at the end of the first leg 2132 and configured to be positioned into the cavity of the wound retractor 2145 to provide gases to the wound. In an embodiment, the first leg 2132 of the interface tube 2130 is at least partially rigid. This may allow the first leg 2132 to be manipulated by the user. The first leg 2132 may comprise a material with a memory property, such that the first leg 2132 remains in a relatively set position after manipulation by the user. The first leg 2132 may be readjusted during use. As a result, the first leg 2132 can be positioned by a user to reduce interference of the first leg 2132 during a procedure.

The second leg 2134 of the interface tube 2130 pneumatically connects with the upper ring 2150 of the wound retractor 2145. The upper ring 2150 may be hollow, and thus, a gases pathway may be provided therein. Thus, gases can flow from the interface tube 2130 and into the upper ring 2150 via the second leg 2134. In an embodiment, the upper ring 2150 may comprise a gases permeable material. This may allow gases to diffuse to the wound edge from the upper ring 2150. In an embodiment, the gases permeable material comprises directed openings.

In an embodiment, the diffuser interface 2135 is configured to be positioned near to the wound edge on the outer side of the wound retractor 2145. In this embodiment, the gases permeable upper ring 2150 is configured to deliver gases to the cavity and the diffuser interface 2135 is configured to deliver gases to the wound edge.

In an embodiment, the upper ring 2150 connects with the second leg 2134 via a connector 2170. The connector 2170 may pneumatically occlude the gases from the second leg 2134. Thus, at least a portion of the connector 2170 comprises a gases permeable region to allow gases to diffuse from the second leg 2134 into the wound edge. In an embodiment, at least a part of the interface tube 2130 comprises a gases permeable material to allow gases to diffuse into the wound edge. In an embodiment, at least a part of the diffuser interface 2135 comprises directed openings to allow gases to diffuse into the wound edge.

Figure 20:
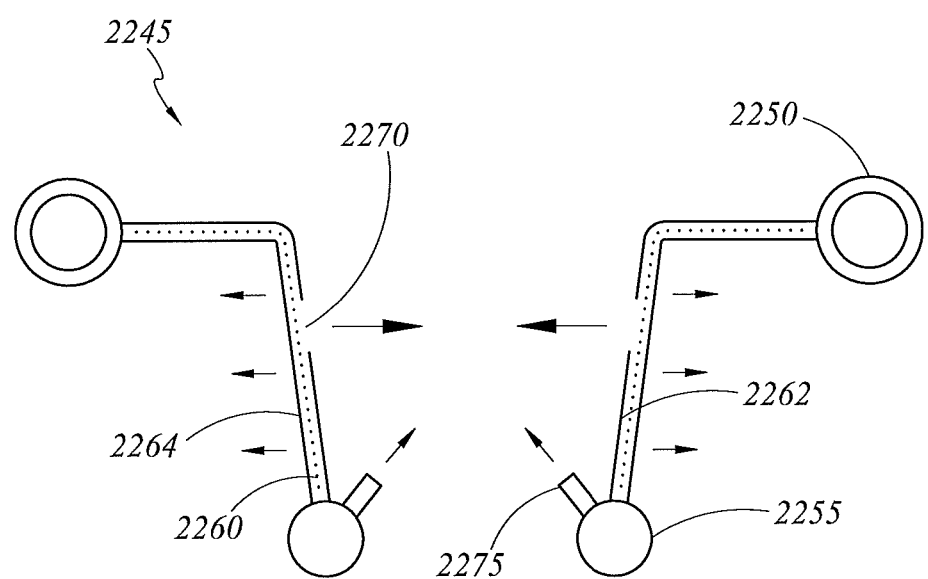
FIG. 20 illustrates a cross-sectional view of a wound retractor with a multi-layer sleeve according to an embodiment of the present disclosure.

The wound retractor 2145 may comprise a sleeve (not shown) similar to those discussed above. Thus, the sleeve can be permeable to gases, which may further facilitate gases transfer between the wound edge and the cavity. In an embodiment, the sleeve may be gases impermeable. The features of the wound retractor 2145 may be integrated into any other wound FIG. 20 illustrates a cross-sectional view of a wound retractor 2245 with a multi-layer sleeve according to an embodiment of the present disclosure. The wound retractor 2245 includes an upper ring 2250, a lower ring 2255, and a sleeve 2260 extending between and connecting the upper ring 2250 and the lower ring 2255. The sleeve 2260 comprises multiple layers, such as, for example, an impermeable film 2262 and a gases permeable material 2264. In an embodiment, the gases permeable material comprises an open cell foam. In the illustrated embodiment, the impermeable film 2262 is adjacent to the cavity (in other words, the impermeable film 2262 is on the inside of the sleeve), while the gases permeable material 2264 is adjacent to the wound edge.

The impermeable film 2262 may include apertures 2270 through which gases can enter the cavity. The apertures 2270 expose the cavity to the gases permeable material 2264. This allows the gases to diffuse through the gases permeable material 2264 and into the cavity.

The upper ring 2250 may be a substantially hollow ring that is configured to receive the gases. Gases can move from the upper ring 2250 to the sleeve 2260. Here, the gases diffuse into the cavity or to the wound edge as discussed. Remaining gases can enter the lower ring 2255 from the sleeve 2260. In an embodiment, the lower ring 2255 is substantially hollow and comprises a gases outlet 2275. The gases outlet 2275 may be configured to move gases from the lower ring 2255 into the cavity.

A gases source may connect with the upper ring 2250 using, for example, a connector. The connector may be configured to provide a pneumatic connection between the gases source and the upper ring 2250. Thus, gases move into the substantially hollow upper ring 2250 and can be distributed to the patient 140.

In an embodiment, the lower ring 2255 is configured to receive the gases from the gases source. Thus, gases move from the lower ring 2255 into the sleeve 2260 and into the substantially hollow upper ring 2250. The apertures 2270 move the gases into the cavity. In an embodiment, both the lower ring 2255 and the upper ring 2250 are configured to receive gases from the gases source.

In an embodiment, the layers of the sleeve 2260 are reversed such that the impermeable film 2262 is adjacent to the wound edge. Thus, the apertures 2270 allow gases to move into the wound edge region. The gases permeable material 2264 is adjacent to the cavity, which allows gases to diffuse into the cavity. The features of the wound retractor 2245 may be integrated into any of the other wound retractors described herein.

Figure 21A:
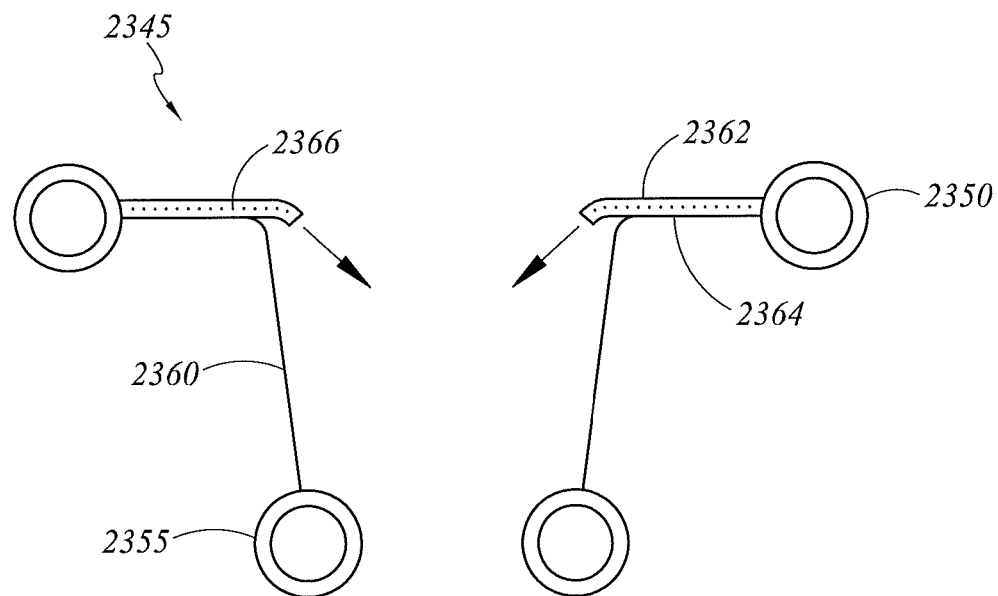
FIGS. 21A and 21B illustrate various views of a wound retractor with an adjustable diffuser according to embodiments of the present disclosure.
Figure 21B:
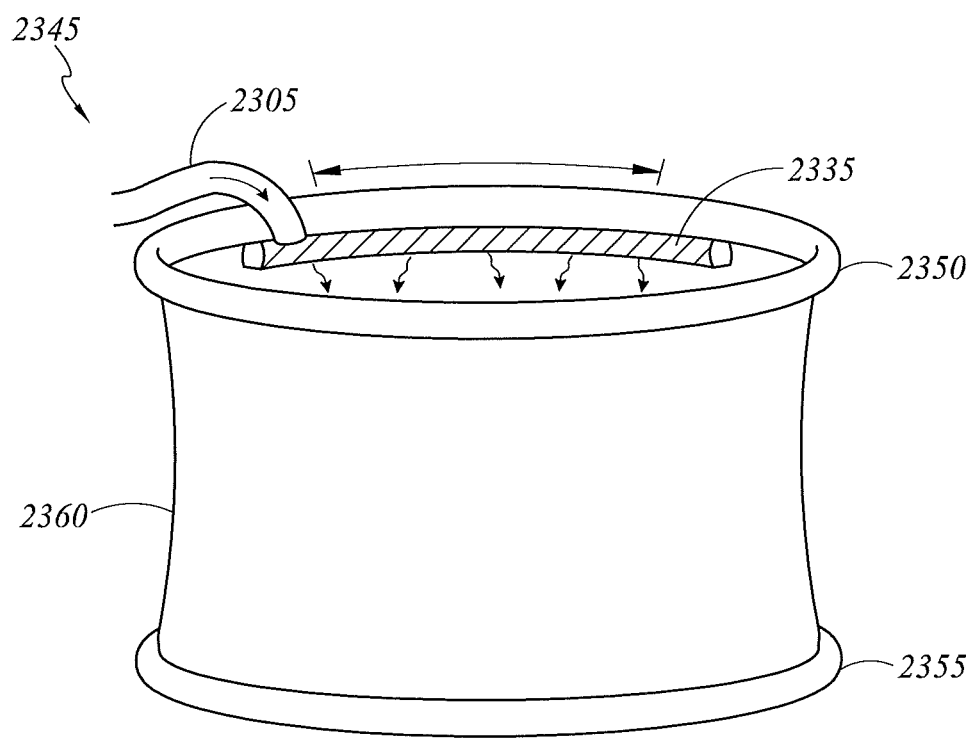

FIGS. 21A and 21B illustrate various views of a wound retractor with an adjustable diffuser according to embodiments of the present disclosure. FIG. 21A illustrates a cross-sectional view of a wound retractor 2345 with a pocket formed between inner and outer sleeve layers. The wound retractor 2345 includes an upper ring 2350, a lower ring 2355, and a sleeve 2360 extending between and connecting the upper ring 235 and the lower ring 2355. The sleeve 2360 comprises an inner layer 2362 and an outer layer 2364 with a pocket 2366 defined therein. The inner layer 2362 and the outer layer 2364 may be configured to be impermeable to gases. The inner layer 2362 is configured to be adjacent to the cavity, while the outer layer 2364 is configured to be adjacent to the wound edge. The inner layer 2362 of the sleeve 2360 may be configured to be torn, cut away, or otherwise removed at or near the wound height. Tearing of the inner layer 2362 exposes the gases permeable material within the pocket 2366 to the cavity. As a result, gases diffuse into the cavity. The inner layer 2362 of the sleeve 2360 may include perforations. The perforations may aid with tearing of the inner layer 2362. The perforations may indicate suitable tear points. Thus, the height of the tear of the inner layer 2362 is customisable to suit different wound heights. FIG. 21A illustrates the wound retractor 2345 with the inner layer 2362 torn away, thus allowing gases to diffuse into the cavity.

In an embodiment, the sleeve 2360 is bifurcated to form a detached portion of the inner layer 2362. The detached portion of the inner layer 2362 may function as a flap that can be torn to expose the gases permeable material within the pocket 2366. Thus, the outer layer 2364 continues to span between the upper ring 2350 and the lower ring 2355 such that the tissues are held in place during the procedure, while the inner layer 2362 only partially spans the distance between the two rings.

The upper ring 2350 may be substantially hollow and may be configured to receive the gases from the gases source as described elsewhere herein. The gases can then diffuse from the upper ring 2350 into the gases permeable material within the pocket 2366, ready to enter the cavity via the torn edge. In an embodiment, a gases outlet is configured to be positioned on the lower ring 2355. The gases outlet can deliver gases to the cavity or to the wound edge.

In an embodiment, the lower ring 2355 is configured to receive gases from the gases source. Thus, the pocket 2366 comprising the gases permeable material is located proximal to the lower ring 2355. The detached portion of the inner layer 2362 is configured to be torn such that gases enter the cavity.

In an embodiment, the outer layer 2364 is configured to be torn to expose the pocket 2366. Thus, the wound edge benefits from the exposure to heated, humidified gases. A gases outlet is positioned on the lower ring 2355 and is configured to deliver gases to the cavity.

FIG. 21B illustrates a perspective view of the wound retractor 2345 that comprises the upper ring 2350, the lower ring 2355, and a sleeve 2360 extending between and connecting the upper ring 2350 and the lower ring 2355. In the illustrated embodiment, the upper ring 2350 is configured to comprise a material impermeable to gases flow. A diffuser interface 2335, such as a conventional diffuser, is configured to couple with the upper ring 2350. The diffuser interface 2335 is configured to be coupled to at least a part of the upper ring 2350. In an embodiment, the diffuser interface 2335 is configured to be coupled to the entirety of the upper ring 2350. Coupling can occur, for example, via adhesives, hook and loop mechanisms, clipping or snap-fitting the diffuser interface 2335 into place, for example, as described elsewhere herein. The coupling can be configured to be removable. In an embodiment, the coupling can be configured to be permanent. In an embodiment, the diffuser interface 2335 can be coupled with, for example, any wound retractor described herein. Thus, the diffuser interface 2335 can be integrated with different wound retraction systems. Coupling between the diffuser interface 2335 and the wound retractor 145 is configured to be quick and simple and to require minimal, if any, training. In an embodiment, the diffuser interface 2335 can be integrated with the upper ring 2350. Thus, the wound retractor 2345 comprises a single component, which can be inserted into the cavity without adaptation.

The diffuser interface 2335 may comprise a gases permeable material, such as, for example, directed openings, a foam or an open cell foam. The diffuser interface 2335 may be configured to be adjustable. For example, the diffuser interface 2335 can be cut or torn depending on the size of the wound. In an embodiment, the diffuser interface 2335 comprises perforations to indicate possible tear locations. In an embodiment, the diffuser interface 2335 can be configured to be torn prior to insertion into the cavity. In an embodiment, the diffuser interface 2335 can be configured to be torn following insertion into the cavity. Gases flow from a gases source 2305 and into the diffuser interface 2335. From here, gases are configured to diffuse into the cavity.

In an embodiment, multiple diffuser interfaces 2335 are provided to the user. The multiple diffuser interfaces 2335 can span a range of sizes. In an embodiment, a larger size may correspond to an increased length. Thus, the diffuser interface 2335 can be chosen to fit the size of the wound.

In an embodiment, the diffuser interface 2335 can be coupled with the lower ring 2355. Thus, the upper ring 2350 can be rolled to provide tension to the sleeve 2360. In an embodiment, the gases source 2305 is positioned within the cavity. In an embodiment, the gases source 2305 is positioned outside of the cavity. The features of the wound retractor 2345 may be integrated into any of the wound retractors described herein.

Figure 22A:
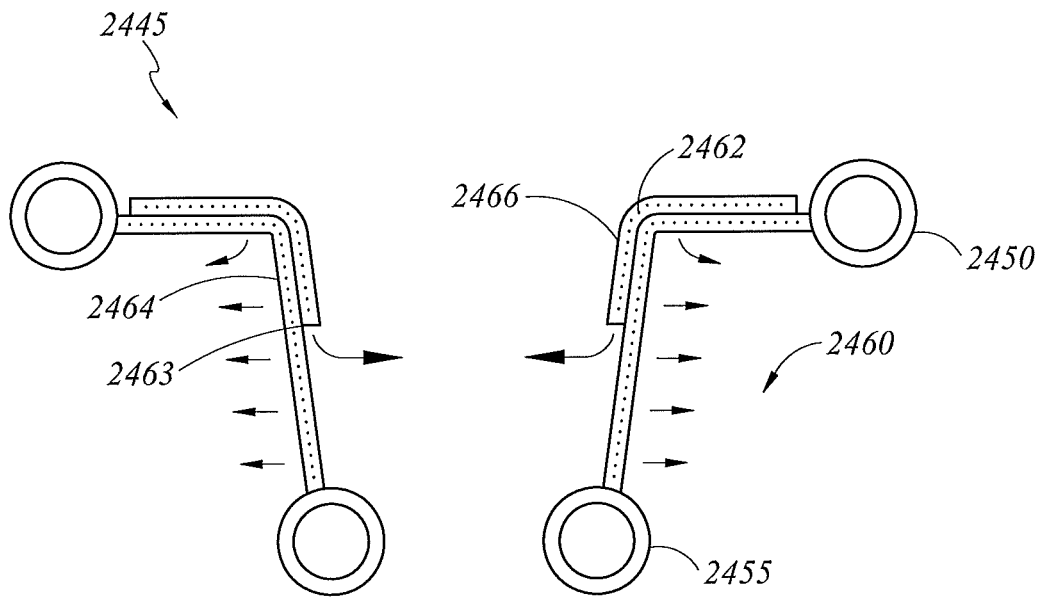
FIGS. 22A and 22B illustrate cross-sectional views of a wound retractor including an inner foam layer configured to contact a wound edge according to embodiments of the present disclosure.
Figure 22B:
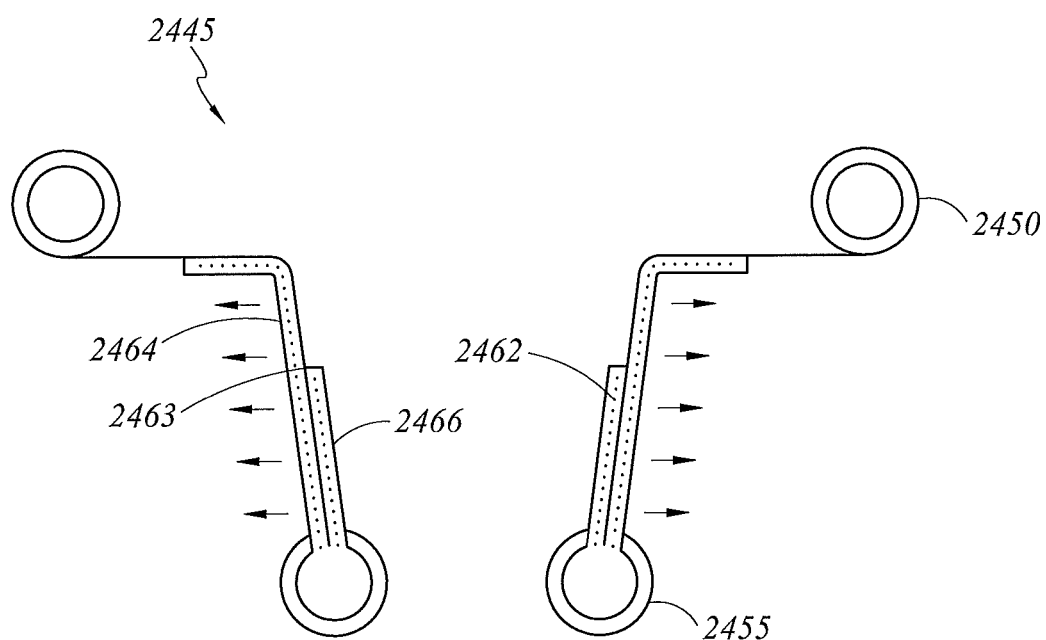

FIGS. 22A and 22B illustrate cross-sectional views of a wound retractor 2445 including an inner foam layer configured to contact a wound edge according to embodiments of the present disclosure. The wound retractor 2445 includes an upper ring 2450, a lower ring 2455, and a sleeve 2460 extending between and connecting the upper ring 2450 and the lower ring 2455. The upper ring 2450 may be substantially hollow and may be configured to receive gases from a gases source. The sleeve 2460 comprises an inner layer 2462 and an outer layer 2464. The inner layer 2462 comprises a film coating or layer 2466. The film coating or layer 2466 may be impermeable to gases. The inner layer 2462 and the outer layer 2464 may comprise a gases permeable material, such as, for example, an open cell foam. Gases within the upper ring 2450 move into the gases permeable material of the inner layer 2462 and the outer layer 2464. Gases within the outer layer 2464 diffuse into the wound edge region. As a result, the wound edge benefits from exposure to heated, humidified gases.

The inner layer 2462 may extend only partially along the outer layer 2464. The inner layer 2462 extends along the outer layer 2464 proximal to the upper ring 2450. In an embodiment, the film coating or layer 2466 coats a single side of the inner layer 2462. As a result, an aperture 2463 of the inner layer 2462 exposes the gases permeable material to the cavity. Gases diffuse through the aperture 2463 into the cavity. The position of the aperture 2463 is chosen to control the position at which the gases are released into the cavity.

FIG. 22B illustrates a cross-sectional view of the wound retractor 2445, wherein the lower ring 2455 is substantially hollow and is configured to receive the gases from the gases source. The inner layer 2462 extends only partially along the outer layer 2464. The inner layer 2462 extends along the outer layer 2464 proximal to the lower ring 2455. Thus, gases enter the wound retractor 2445 at the lower ring 2455 and diffuse into the gases permeable material of the inner layer 2462 and the outer layer 2464 of the sleeve 2460. The aperture 2463 of the inner layer 2462 exposes the gases permeable material to the cavity. Thus, gases diffuse from the gases permeable material into the cavity.

In the illustrated embodiment, the upper ring 2450 can be rolled into position, such that the sleeve 2460 is under tension during the procedure. This results in the sleeve 2460 sufficiently holding the tissue in place during the procedure. The features of the wound retractor 2445 may be integrated into any of the wound retractors described herein.

Figure 23:
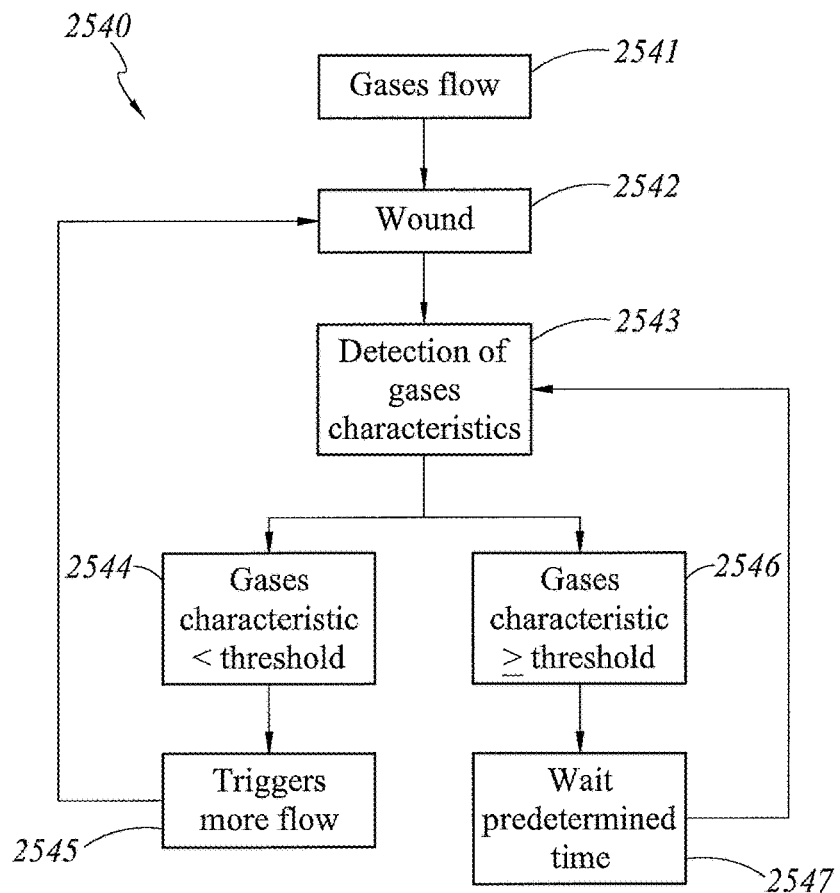
FIG. 23 illustrates a flow chart of a method implemented by a control system for controlling gases flow to a wound according to an embodiment of the present disclosure.

FIG. 23 illustrates a flow chart of a method implemented by a control system 2540 for controlling gases flow to a wound 2542 according to an embodiment of the present disclosure. The control system 2540 includes multiple steps that heat and humidify the wound 2542. At block 2541, gases flow into the wound 2452. The gases may be distributed using any of the wound retractors described herein. A sensor is positioned within the cavity. The sensor may be located on, for example, an interface or a wound retractor. The sensor is configured to determine a characteristic of the gases flow at block 2543. The control system 2540 determines if the measured characteristic is above a predetermined threshold at block 2546 or below a predetermined threshold at block 2544. If the characteristic is below a predetermined threshold, such as that shown at 2544, the control system triggers more flow 2545 to enter the wound 2542. Following additional flow into the wound 2542, the control system 2540 continues to detect the characteristic of the gases flow. In an embodiment, the control system 2540 is configured to wait a predetermined period of time before determining a characteristic of the gases 2543 via the sensor, following the triggering of more flow 2545. In an embodiment, the control system 2540 controls the flow 2545 by comparing a predetermined threshold to another characteristic of the system, such as the type and/or size of wound retractor or diffuser in use, which could be determined automatically or via user input.

Alternatively, following detection of the gases characteristic at 2543, the gases characteristic may be determined to be equal to or greater than a predetermined threshold, such as at block 2546, for example. In this instance, the control system 2540 is configured to wait a predetermined time 2547 before returning to 2543 to detect a characteristic of the gases flow. Thus, determination and feedback regarding the characteristic of the gases flow uses closed loop control in at least one configuration.

In an embodiment, the sensor is configured to determine a concentration of the gases. Thus, the control system 2540 is configured to regulate the gases flow based on the gases concentration. In an embodiment, the predetermined threshold of the concentration of the gases flow may be, for example, between 50%-100%. In an embodiment, the predetermined threshold of the concentration of the gases flow may be between 75%-100%. In an embodiment, the predetermined threshold of the concentration of the gases flow may be between 50%-75%. In an embodiment, the predetermined threshold of the concentration of the gases flow may be between 75%-90%. In an embodiment, the predetermined threshold of the concentration of the gases flow may be between 90%-100%. In some instances, a higher gases concentration may be more beneficial to the patient 140.

In an embodiment, multiple sensors are configured to determine concentrations of different gases. For example, a sensor may be configured to regulate the flow of carbon dioxide ($CO_2$) using any of the predetermined concentration thresholds described above. In an embodiment, another sensor may be configured to regulate the flow of oxygen ($O_2$) or nitrous oxide ($N_2O$) using a predetermined concentration threshold between 0%-5%. In an embodiment, the predetermined threshold of the concentration of $O_2$ or $N_2O$ may be between 5%-50%.

The predetermined time may be configured to be anywhere between 1 and 30 minutes. More preferably, the predetermined time may be between 1 and 10 minutes. In an embodiment, the predetermined time is less than 1 minute, for example, 10 seconds or 30 seconds. It is to be understood that different time periods also fall within the scope of the disclosed apparatus and systems. Any of the wound retractors described herein may be used with the control system 2540.

Figure 24:
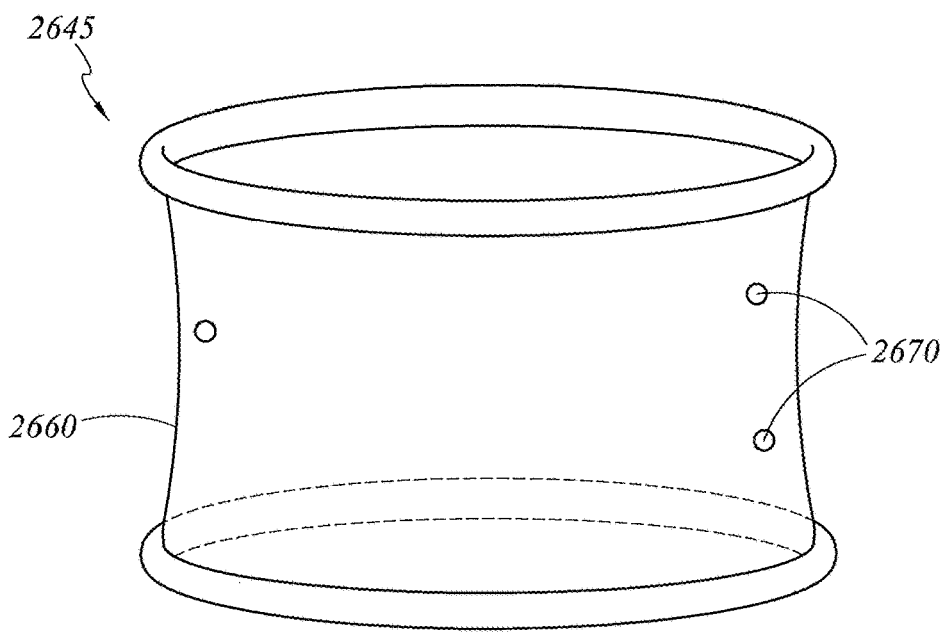
FIG. 24 illustrates a perspective view of a wound retractor including sensors controlled using the control system of FIG. 23 for measuring a characteristic of gases within a cavity according to an embodiment of the present disclosure.

FIG. 24 illustrates a perspective view of a wound retractor 2645 including sensors controlled using the control system of FIG. 23 according to an embodiment of the present disclosure. The wound retractor 2645 comprises a sensor 2670 configured to detect a characteristic of the gases flow. The sensor 2670 may detect, for example, tissue oxygen concentration using direct measurements, such as, for example, a tissue oxygen probe, or using indirect measurements, such as, for example, by gases concentration, humidity or gases temperature. The control system 2540 may use the sensed characteristic to determine if the characteristic is equal to or above a predetermined threshold 2546. The control system 2540 may actuate a control pathway to ensure the characteristic meets the threshold condition.

If the sensor 2670 is configured to detect a concentration of the gases flow, or tissue oxygenation concentration, the control system 2540 can cause additional flow to enter the cavity. In an embodiment, multiple sensors 2670 can be used to determine a single characteristic of the gases flow, or multiple characteristics of the gases flow.

For example, if the characteristic identified by the sensor is temperature, and the temperature is determined to be below a predetermined threshold, the control system 2540 may activate additional heating. The heating may take the form of active heating mechanisms, an exothermic reaction from a chemical source, or passive heating mechanisms, such as body heat, for example. An example of an active heating mechanism is a heater wire. The heater wire connects with an external power supply. Heat through the heater wire can be controlled via the control system 2540.

In an additional example, a humidity sensor determines the humidity of the gases. If the humidity is determined to be below a desired threshold, the dew point temperature of the gases is increased. In an embodiment, this occurs by increasing the temperature of the water within the humidification chamber 120. Alternatively, if the humidity sensor determines that the humidity is above a desired threshold, the dew point temperature of the gases is decreased. Thus, for example, the temperature of the water within the humidification chamber 120 is decreased.

In an embodiment, chemicals could be used to generate an exothermic reaction. For example, an exothermic reaction could be generated using a supersaturated solution of sodium acetate in water. The heat produced by the reaction could be controlled by controlling the amount of reacting chemicals. For example, the wound retractor 2645 may comprise a sleeve 2660 that is coated with a chemical layer. The sleeve 2660 may be segmented such that chemicals can be contained within different segments. Thus, different segments may be actuated at different times to control the rate of the reaction. Actuation of the chemical layer may comprise gases or chemicals contacting the chemical layer.

In an embodiment, the control system 2540 can be configured to connect with the sensor 2670 via a wired connection or a wireless connection. The control system 2540 can be an external component to the wound retractor 2645. In an embodiment, the control system 2540 can be configured to removably couple with the wound retractor 2645. In an embodiment, the control system 2540 can permanently couple with the wound retractor 2645. In an embodiment, the control system 2540 can be integrated into the wound retractor 2645.

Figure 25:
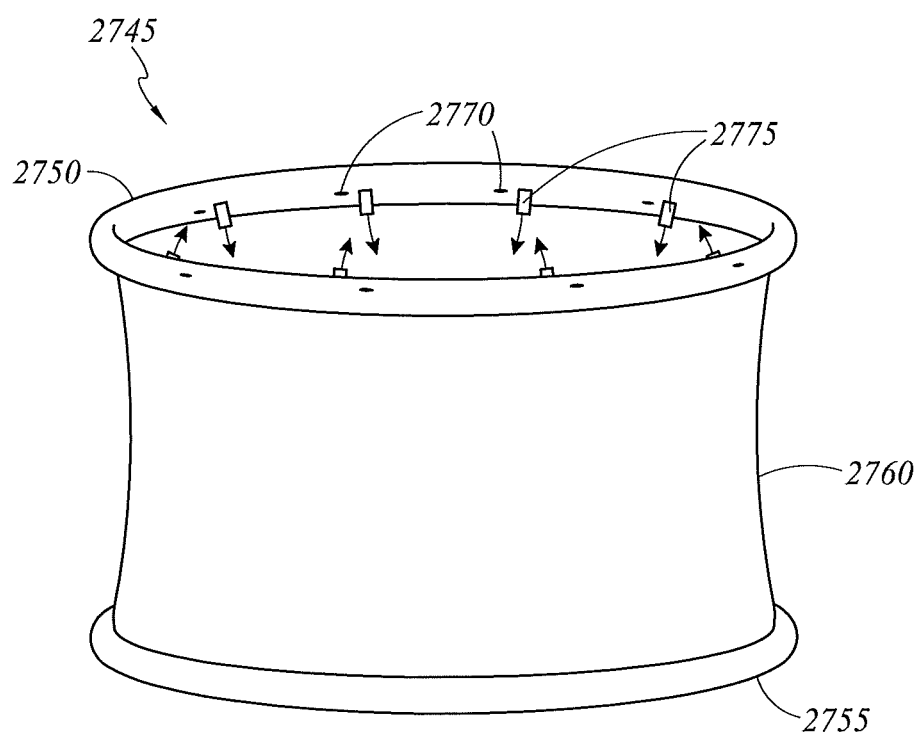
FIG. 25 illustrates a perspective view of a wound retractor including a plurality of sensors and a plurality of independently controllable gases outlets according to an embodiment of the present disclosure.

FIG. 25 illustrates a perspective view of a wound retractor 2745 that is configured with multiple sensors 2770 according to an embodiment of the present disclosure. The wound retractor 2745 includes an upper ring 2750, a lower ring 2755, and a sleeve 2760 extending between and connecting the upper ring 2750 and the lower ring 2755. The wound retractor 2745 also includes a plurality of sensors 2770. In an embodiment, a single sensor 2770 is used. The sensors 2770 can be integrated into the upper ring 2750. The sensors 2770 can be configured to sense a characteristic at different regions of the upper ring 2750. In an embodiment, the sensors 2770 are, for example, an accelerometer or a gyroscope. Hence, the sensors 2770 can be used to determine the orientation of the upper ring 2750. Each of the sensors 2770 may be independently coupled with a control system, for example the control system 2540 described above. The control system may enable selective diffusion of gases into the cavity with regards to orientation.

In the illustrated embodiment, the upper ring 2750 is integrated with an interface. The upper ring 2750 can, therefore, diffuse gases into the cavity. In an embodiment, the upper ring 2750 comprises a gases permeable material, for example, directed openings, such that the gases can be diffused into the cavity. In an embodiment, the upper ring 2750 comprises multiple gases outlets 2775 that can be independently controlled. Thus, gases delivery into the cavity can be optimised for different orientations or changes during the procedure in the orientation of the wound retractor 2745. This may lead to more specific gases delivery, and thus, also reduce wastage of gases. For example, the gases may be delivered to the highest point of the wound retractor 2745 to improve filling of the cavity.

In an embodiment, the gases outlets 2775 may comprise valves, such as, for example, float valves. The valves may actuate at different orientations due to the quantity of gases present at or near the valve. Thus, the valves comprise a passively actuating system through which gases can differentially enter the cavity.

In an embodiment, the gases outlets 2775 can be positioned within the sleeve 2760 of the wound retractor 2745. In an embodiment, the gases outlets 2775 can be positioned on the lower ring 2755. In an embodiment, the gases outlets 2775 can be positioned on a ring-shaped diffuser that can be clipped onto the wound retractor 2745, similar to the ring-shaped diffuser interface 535. These embodiments have the added benefit that the upper ring 2750 can be rolled to tension the sleeve 2760 without impacting the gases delivery into the cavity. The features of the wound retractor 2745 may be integrated with any of the wound retractors described herein.

Figure 26A:
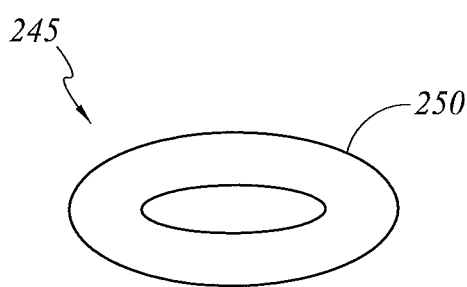
FIGS. 26A and 26B illustrate perspective views of an upper ring of a wound retractor in a first state and a second state according to embodiments of the present disclosure.
Figure 26B:
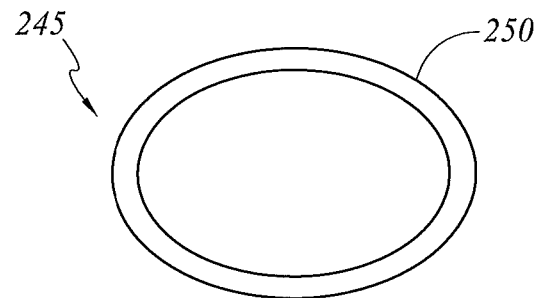

FIGS. 26A and 26B illustrate perspective views of a wound retractor 245 comprising an upper ring 250 that has a first state and a second state according to embodiments of the present disclosure. In an embodiment, the upper ring 250 comprises a material that changes shape when stimulated with an electric field, such as an electroactive polymer. Upon stimulation with an electric field, the upper ring 250 moves from the first state, as illustrated in FIG. 26A, to the second state, as illustrated in FIG. 26B. In the first state, the upper ring 250 may be flexible and pliable. In the second state, the upper ring 250 may be substantially rigid. In the second state, the upper ring 250 may pull the sleeve (not shown) taut, retracting the wound to create the cavity. The stimulation with an electric field can be performed following insertion of the wound retractor 245 into the cavity. The electric field can be created using a power source (not shown). In an embodiment, the power source may be external to the wound retractor 245. In an embodiment, the power source may be integrated with the wound retractor 245.

In an embodiment, the electric charge is continuously applied to the upper ring 250 to maintain the second state within the cavity. Once the electric charge is removed, the upper ring 250 reverts back to the first state. In an embodiment, the electric charge may be discretely applied to move the upper ring 250 from the first state to the second state. A sequential application of electric charge may cause the upper ring 250 to revert to the first state.

Although the upper ring 250 is illustrated in FIGS. 26A and 26B, the same principles described herein may be applied to a lower ring alternatively or additionally.

Figure 27:
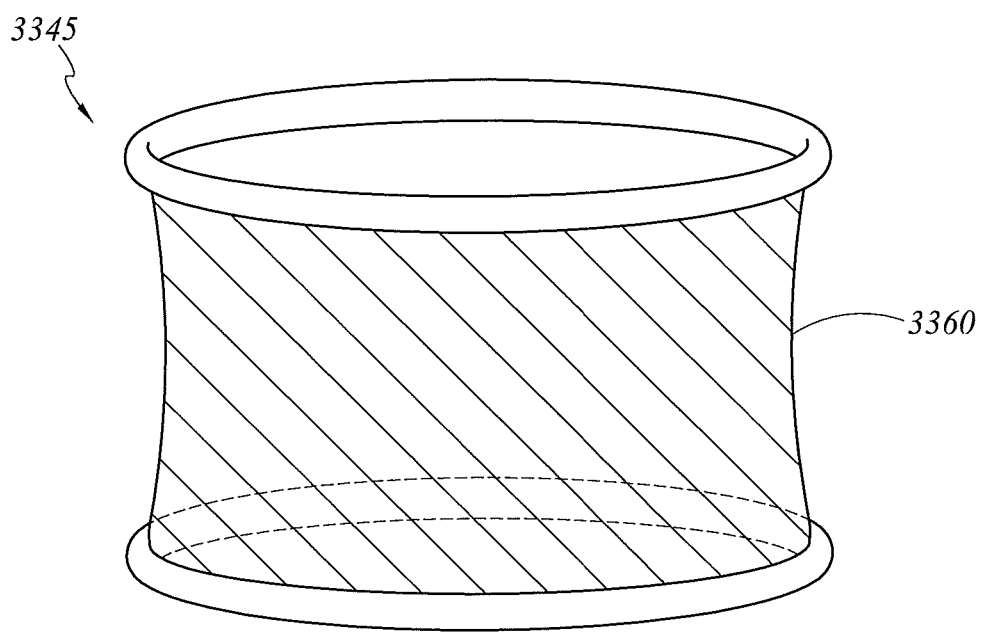
FIG. 27 illustrates a perspective view of a wound retractor including a sleeve comprising a temperature responsive material according to an embodiment of the present disclosure.

FIG. 27 illustrates a perspective view of a wound retractor 3345 including a sleeve 3360 comprising a temperature responsive material, such as, for example, a heat shrink material, according to an embodiment of the present disclosure. The sleeve 3360 can comprise a polymeric material, such as fluoropolymers, elastomers, silicone, or polyolefins. The materials can be configured such that the sleeve 3360 shrinks in response to body heat, such as, for example, upon contact with the wound edge. In an embodiment, the sleeve 3360 can be configured to shrink due to heating of a heater wire that is coupled with the sleeve 3360. The heating wire may be embedded into the sleeve 3360 or positioned on the surface thereof. In an embodiment, a chemical reaction between the sleeve 3360 and the wound edge may cause the sleeve 360 to retract.

In an embodiment, the materials can be configured to shrink solely along a single axis, for example, either radially or longitudinally. In an embodiment, the materials can be configured to shrink more along one axis than another. This may be achieved due to the orientation of the fibres within the sleeve 3360, the weave of the sleeve 3360, or the properties of the materials used, such as, for example, an anisotropic material. In an embodiment, this axis is the longitudinal axis. Shrinkage of the sleeve 3360 may apply tension such that the cavity is created and maintained within the body.

Figure 28A:
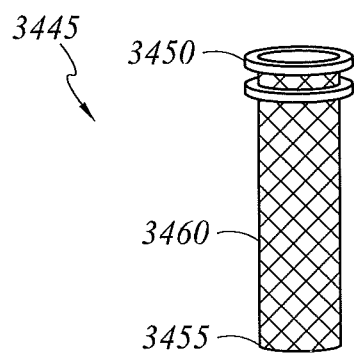
FIGS. 28A and 28B illustrate perspective views of a wound retractor in a first state and a second state according to embodiments of the present disclosure.
Figure 28B:
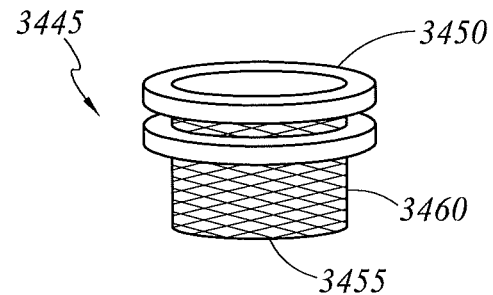

FIGS. 28A and 28B illustrate perspective views of a wound retractor 3445 according to embodiments of the present disclosure. The wound retractor 3445 comprises an upper ring 3450, a lower ring 3455, and a sleeve 3460 extending between and connecting the upper ring 3450 and the lower ring 3455. The upper ring 3450 comprises a first state, as illustrated in FIG. 28A, and a second state, as illustrated in FIG. 28B. In an embodiment, the sleeve 3460 is permeable to gases and liquids. In an embodiment, the sleeve 3460 is impermeable to gases. In the first state, the upper ring 3450 comprises a coiled, compressed or dissembled state. To move from the first state to the second state, the upper ring 3450 is manipulated or assembled such that it clicks into place. In an embodiment, the mechanism to move the wound retractor 3445 from the first state 3452 to the second state 3454 comprises a reversible snap-fit mechanism or other mechanism that is easily actuated by a user. The second state is an expanded state for use within the cavity. The expanded state pushes back the wound edge, thereby creating the cavity. This increases access to the wound.

To remove the wound retractor 3445, the upper ring 3450 is manipulated back into the first state and withdrawn from the cavity. In the illustrated embodiment, the first state is smaller in size when compared with the second state. The upper ring 3450 in the first state is more easily manipulated through confined spaces. The sleeve 3460 comprises a flexible material that is stretched from the first state to the second state.

Figure 29A:
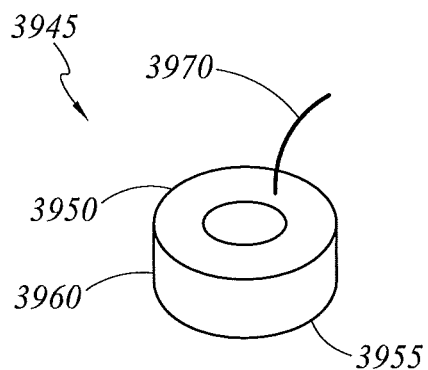
FIGS. 29A through 29E illustrate various views of a wound retractor that can transition between a first state and a second state by use of a tether according to embodiments of the present disclosure.
Figure 29B:
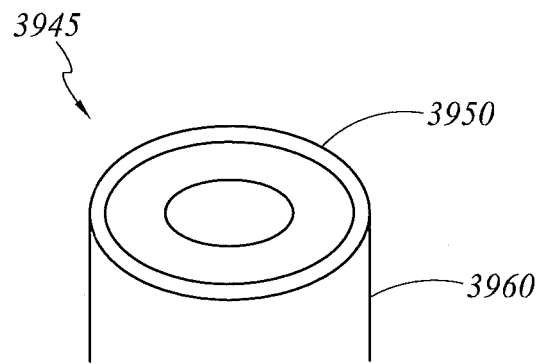
Figure 29C:
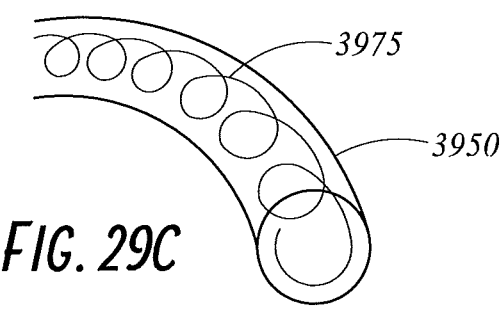

FIGS. 29A through 29E illustrate various views of a wound retractor 3945 that can transition between a first state and a second state by use of a tether according to embodiments of the present disclosure. The wound retractor 3945 comprises an upper ring 3950, a lower ring 3955, and a tether 3970. The lower ring 3955 is a rigid structure. The upper ring 3950 comprises a biasing mechanism, such as, for example, a spring 3975. The spring 3975 is compressed in a first state, as illustrated in FIG. 29A. Thus, in the first state, the upper ring 3950 may have a compressed and reduced in size compared with, for example, the upper ring 150, and with a second state, as illustrated in FIG. 29B. The tether 3970 is coupled with the upper ring 3950 and holds the spring 3975 in the first state.

To move the upper ring 3950 from the first state to the second state, the tether 3970 is pulled, disengaged, torn, or otherwise removed from the spring 3975. This releases the spring 3975, causing the upper ring 3950 to expand, providing sufficient workspace for the surgeon. The second state provides a state in which tension is applied to a sleeve 3960 to sufficiently retract the tissues within the cavity. In an embodiment, the tether 3970 comprises a cord or tab. The tether 3970 is configured to be pulled, activating the second state, following insertion of the wound retractor 3945 into the cavity.

Figure 29D:
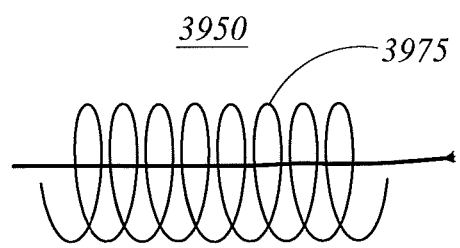
Figure 29E:
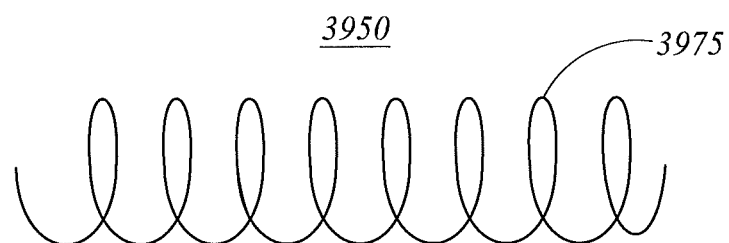

The upper ring 3950 comprises a soft material which is flexible such that it can move between the first state and the second state. The spring 3975 is coiled within the upper ring 3950, as illustrated in the cross-section of FIG. 29C. FIGS. 29D and 29E qualitatively show the change in pitch that occurs as the spring 3975 moves between the first state and the second state. Although the previous description describes the upper ring 2950, it could equally be applied to a lower ring of a wound retractor.

Figure 30A:
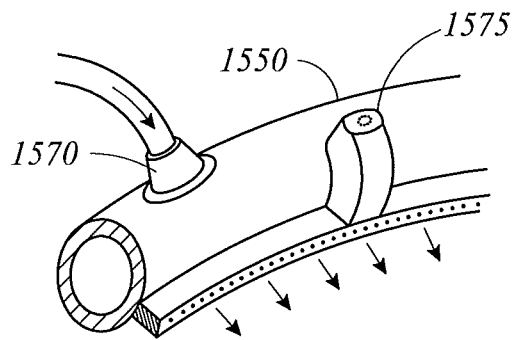
FIGS. 30A through 30C illustrate various views of a wound retractor including an inflatable upper ring and an inflatable lower ring according to embodiments of the present disclosure.
Figure 30B:
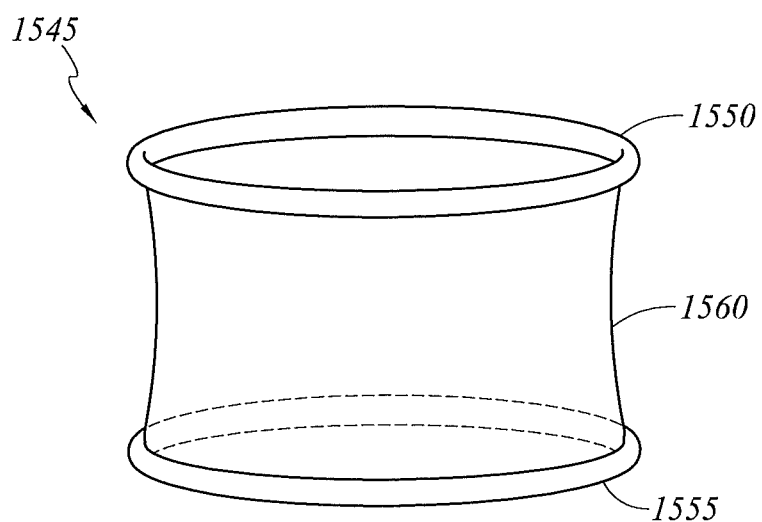
Figure 30C:
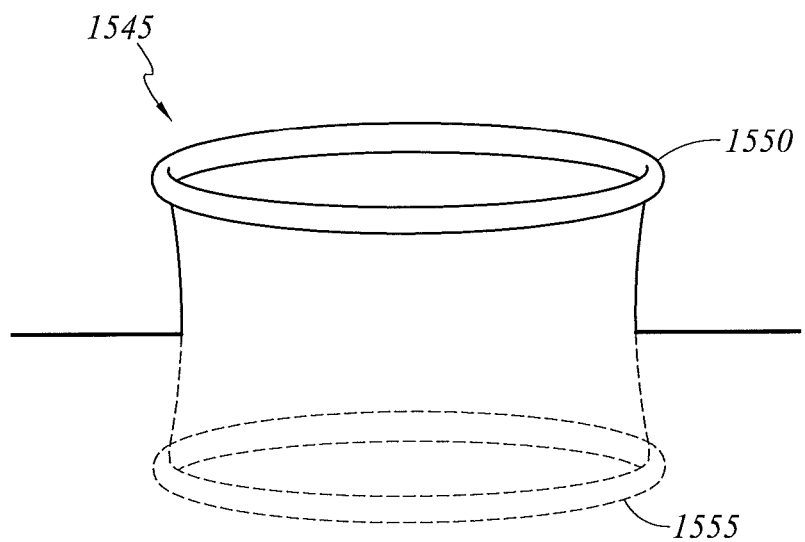

FIGS. 30A through 30C illustrate various views of a wound retractor 1545 including an inflatable upper ring and an inflatable lower ring according to embodiments of the present disclosure. The wound retractor 1545 comprises an upper ring 1550, a lower ring 1555, and a sleeve 1560 extending between and connecting the upper ring 1550 and the lower ring 1555. Gases are provided to the wound retractor 1545 from a gases source. The upper ring 1550 and the lower ring 1555 each comprise flexible, hollow rings that are configured to be inflated by the gases. The upper ring 1550 and the lower ring 1555 each comprise a gases inlet 1570. FIG. 17A illustrates an example wherein the upper ring 1550 comprises the gases inlet 1570. The gases inlet 1570 can take the form of a valve, such as, for example, a one-way valve, to allow entry of the gases.

The upper ring 1550 and the lower ring 1555 each comprises a first state, as illustrated in FIG. 17B, and a second state, as illustrated in FIG. 17C. The upper ring 1550 and the lower ring 1555 are uninflated in the first state. Inflation of the upper ring 1550 and the lower ring 1555 occurs in the second state. The second state causes the sleeve 1560 to become taut, such that the tissues are sufficiently retracted. Gases entering the upper ring 1550 and the lower ring 1555 via the gases inlet 1570 cause the upper ring 1550 and the lower ring 1555 to move from the first state to the second state.

In an embodiment, a valve 1575 allows the gases to diffuse into the cavity. In an embodiment, the upper ring 1550 and the lower ring 1555 each at least partially comprises a gases permeable material to allow the gases to diffuse into the cavity and the wound edge. In an embodiment, the valve 1575 can be used in combination with the gases permeable material to allow gases to move between the upper ring 1550 and the lower ring 1555 and into the cavity and the wound edge.

The second state creates additional wound depth, thus increasing the height of the cavity. This increases the amount of gases that can be held within the cavity. The upper ring 1550 comprises a flexible material that remains soft and pliable in the second state. This allows the surgeon to manipulate the upper ring 1550 in use, even in the second state.

In an embodiment, the valve 1575 is on one of the upper ring 1550 and the lower ring 1555. For example, the valve 1575 may be on the lower ring 1555 such that gases are diffused into the cavity from the lower ring 1555. In a second example, the valve 1575 may be on the upper ring 1550 such that the gases diffuse into the cavity from the upper ring 1550.

The wound retractor 1545 is inserted into the cavity in the first state. Thus, the wound retractor 1545 is inserted into the cavity prior to inflation of the upper ring 1550 and the lower ring 1555 and, thus, before tension has been applied to the sleeve 1560. As a result, the wound retractor 1545 is easily manipulated and is simple to install. Once installed, the gases source can be connected to the gases inlet 1570, causing the upper ring 1550 and the lower ring 1555 to enter the second state. Removal of the gases source 105 causes the upper ring 1550 and the lower ring 1555 to revert to the first state 1580. Thus, the wound retractor 1545 is removed from the cavity in the first state. This allows for easy removal of the wound retractor 1545.

In an embodiment, only the upper ring 1550 moves between the first state and the second state. In an embodiment, only the lower ring 1555 moves between the first state and the second state. In an embodiment, the upper ring 1550, the lower ring 1555, and the sleeve 1560 are inflated within the cavity upon connection to the gases source. The sleeve 1560 may be pneumatically coupled with the upper ring 1550 and the lower ring 1555. Gases may be diffused to the cavity and the wound edge as described above. In an embodiment, the sleeve 1560 comprises a gases permeable material such that gases diffuse into the cavity. In an embodiment, the sleeve 1560 comprises a gases permeable material such that gases diffuse into the wound edge. In an embodiment, the sleeve 1560 comprises a gases permeable material such that gases diffuse into both the cavity and the wound edge.

Figure 31:
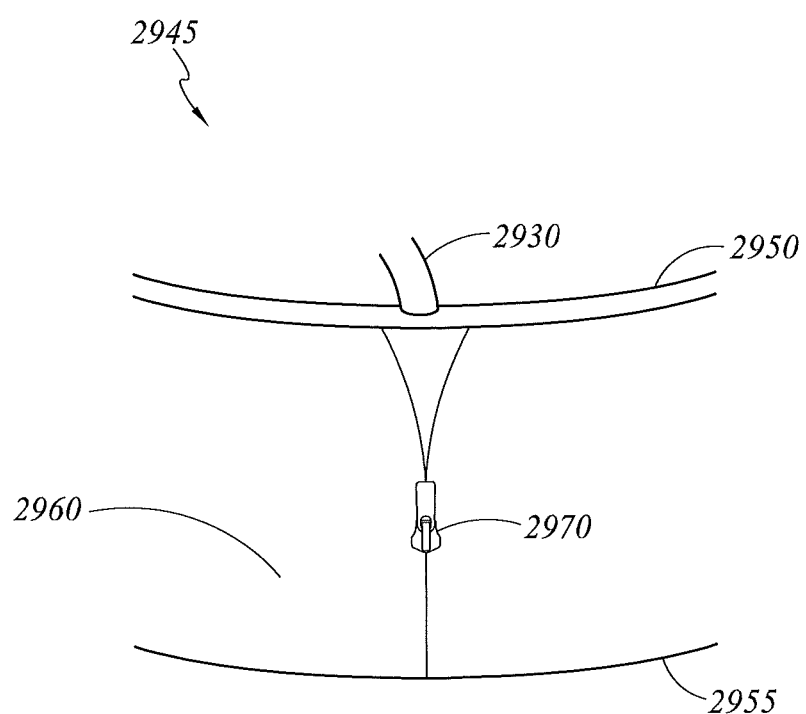
FIG. 31 illustrates a partial perspective view of a wound retractor including a zipper on the sleeve according to an embodiment of the present disclosure.

FIG. 31 illustrates a partial perspective view of a wound retractor 2945 including a zipper on the sleeve according to an embodiment of the present disclosure. The wound retractor 2945 comprises an upper ring 2950, a lower ring 2955, and a sleeve 2960 extending between and connecting the upper ring 2950 and the lower ring 2955. A coupling mechanism extends between the upper ring 2950 and the lower ring 2955. In an embodiment, the coupling mechanism comprises a tongue and groove mechanism or a zipper 2970. In an embodiment, the coupling mechanism comprises a button arrangement or a press seal mechanism.

The zipper 2970 comprises a partially open state and a closed state. The partially open state occurs proximal to the upper ring 2950. The partially opened state exposes at least a part of the cavity to the ambient. While in the closed state the wound retractor 2945 resembles, for example, the wound retractor 145.

The partially open state improves usability of the wound retractor 2945. The upper ring 2950 is configured to be rolled to provide tension to the sleeve 2960. Thus, the partially open state provides access to the upper ring 2950 while rolled. For example, an interface tube 2930 may connect with a gases outlet within the upper ring 2950. Gases may be supplied to the cavity from the gases outlet. A passage exists and remains open between the gases outlet and the cavity. The passage exists between the folds of the upper ring 2950 and the exposure to the wound that is caused by the partially open state. This passage remains open even when the upper ring 2950 is rolled into place. Thus, the user can arrange the wound retractor 2945 to fit the wound while gases movement continues between the interface tube 2930 and the cavity via the gases outlet.

In an embodiment, the gases outlet is configured to be positioned on the zipper 2970. In an embodiment, the gases outlet is permanently positioned on the zipper 2970, for example, via adhesives or welding. In an embodiment, the gases outlet is integral to the zipper 2970. In an embodiment, the gases outlet is removably coupled with the zipper 2970, for example, by a clip or a hook and loop mechanism. Thus, gases are released from the gases outlet positioned on the zipper 2970, into the cavity. In an embodiment, the gases outlet is configured to release gases into the wound edge region. In an embodiment, the gases outlet is configured to release gases to both the wound edge region and the cavity.

The zipper 2970 may be adjusted to suit the size or height of the wound. Thus, gases are delivered near the wound.

In an embodiment, the sleeve 2960 is impermeable to gases. In an embodiment, the sleeve 2960 is permeable to gases. Thus, gases are provided to the wound edge and also to the cavity. In an embodiment wherein the gases outlet delivers gases to the wound edge, a gases permeable embodiment of the sleeve 2960 enables gases to also be delivered to the cavity.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

Unless the context clearly requires otherwise, throughout the description and the claims, the words "comprise," "comprising," and the like, are to be construed in an inclusive sense as opposed to an exclusive or exhaustive sense, that is to say, in the sense of "including, but not limited to."

The disclosed apparatus and systems may also be said broadly to consist in the parts, elements, and features referred to or indicated in the specification of the application, individually or collectively, in any or all combinations of two or more of said parts, elements, or feature.

It should be noted that various changes and modifications to the embodiments described in the present disclosure will be apparent to those skilled in the art. Such changes and modifications may be made without departing from the spirit and scope of the disclosed apparatus and systems and without diminishing its attendant advantages. For instance, various components may be repositioned as desired. Moreover, features from different embodiments may be combined as desired. It is therefore intended that such changes and modifications be included within the scope of the disclosed apparatus and systems. Moreover, not all of the features, aspects, and advantages are necessarily required to practice the disclosed apparatus and systems. Accordingly, the scope of the disclosed apparatus and systems is intended to be defined only by the claims that follow.

What is claimed is:

1. A wound retractor configured to be inserted into a wound opening of a body cavity of a patient, the wound retractor comprising:
   an upper ring;
   a lower ring; and
   a sleeve extending between and connecting the upper ring to the lower ring, wherein the sleeve comprises:
      a gases impermeable layer, wherein the gases impermeable layer is on an inner side of the sleeve such that the gases impermeable layer is configured to face the body cavity, and wherein the gases impermeable layer comprises at least one aperture, the at least one aperture configured to allow gases to enter the body cavity, and
      a gases permeable layer.

2. The wound retractor of claim 1, wherein the gases permeable layer comprises an open cell foam.

3. The wound retractor of claim 1, wherein the gases permeable layer is on an outer side of the sleeve such that the gases permeable layer is configured to face the wound opening.

4. The wound retractor of claim 1, wherein the gases permeable layer is on an inner side of the sleeve such that the gases permeable layer is configured to face the body cavity.

5. The wound retractor of claim 1, wherein the gases impermeable layer is on an outer side of the sleeve such that the gases impermeable layer is configured to face the wound opening.

6. The wound retractor of claim 1, wherein one or both of the upper ring or the lower ring are configured to receive gases from a gases source.

7. The wound retractor of claim 6, wherein the upper ring comprises a connector configured to operably provide a pneumatic connection between the gases source and the upper ring.

8. The wound retractor of claim 1, wherein one or both of the upper ring or the lower ring are substantially hollow.

9. The wound retractor of claim 1, wherein gases are configured to move between the upper and lower rings via the sleeve.

10. The wound retractor of claim 1, wherein the lower ring comprises a gases outlet configured to allow gases to move from the lower ring into the body cavity.

11. The wound retractor of claim 1, wherein the gases impermeable layer extends partially along the gases permeable layer.

12. The wound retractor of claim 1, wherein the gases impermeable layer comprises a film coating.

13. A gases delivery system for use during a surgical procedure on a patient, the system comprising:
   a gases source configured to provide gases;
   a humidifier configured to heat and humidify the gases provided by the gases source; and
   a wound retractor configured to be inserted into a wound opening of a body cavity of the patient to deliver the heated and humidified gases to the patient, the wound retractor comprising:

an upper ring;
a lower ring; and
a sleeve extending between and connecting the upper ring to the lower ring, wherein the sleeve comprises:
a gases impermeable layer, wherein the gases impermeable layer is on an inner side of the sleeve such that the gases impermeable layer is configured to face the body cavity, and wherein the gases impermeable layer comprises at least one aperture, the at least one aperture configured to allow the gases to enter the body cavity, and
a gases permeable layer.

14. The gases delivery system of claim 13, wherein the gases permeable layer comprises an open cell foam.

15. The gases delivery system of claim 13, wherein the gases permeable layer is on an outer side of the sleeve such that the gases permeable layer is configured to face the wound opening.

16. The gases delivery system of claim 13, wherein the gases permeable layer is on an inner side of the sleeve such that the gases permeable layer is configured to face the body cavity.

17. The gases delivery system of claim 13, wherein the gases impermeable layer is on an outer side of the sleeve such that the gases impermeable layer is configured to face the wound opening.

18. The gases delivery system of claim 13, wherein one or both of the upper ring or the lower ring are configured to receive the gases.

19. The gases delivery system of claim 18, wherein the upper ring comprises a connector configured to operably provide a pneumatic connection between the humidifier and the upper ring.

20. The gases delivery system of claim 13, wherein one or both of the upper ring or the lower ring are substantially hollow.

21. The gases delivery system of claim 20, wherein the gases are configured to move between the upper and lower rings via the sleeve.

22. The gases delivery system of claim 13, wherein the lower ring comprises a gases outlet configured to allow the gases to move from the lower ring into the body cavity.

23. The gases delivery system of claim 13, wherein the gases impermeable layer extends partially along the gases permeable layer.

24. The gases delivery system of claim 13, wherein the gases impermeable layer comprises a film coating.

* * * * *